United States Patent
Berner

(10) Patent No.: US 10,285,379 B2
(45) Date of Patent: May 14, 2019

(54) APPARATUS AND METHODS FOR TISSUE SAMPLING AND IDENTITY-TAG ATTACHMENT

(71) Applicant: PRIONICS AG, Schlieren (CH)

(72) Inventor: Alexander Berner, Dachau (DE)

(73) Assignee: PRIONICS AG, Zurich (CH)

(*) Notice: Subject to any disclaimer, the term of this patent is extended or adjusted under 35 U.S.C. 154(b) by 550 days.

(21) Appl. No.: 14/979,815

(22) Filed: Dec. 28, 2015

(65) Prior Publication Data
US 2016/0192621 A1    Jul. 7, 2016

Related U.S. Application Data

(60) Provisional application No. 62/099,416, filed on Jan. 2, 2015.

(51) Int. Cl.
*A01K 11/00* (2006.01)
*A61B 10/02* (2006.01)

(52) U.S. Cl.
CPC .......... *A01K 11/003* (2013.01); *A01K 11/002* (2013.01); *A61B 10/0266* (2013.01)

(58) Field of Classification Search
CPC .................. A01K 11/003; A61B 10/0266
See application file for complete search history.

(56) References Cited

U.S. PATENT DOCUMENTS

| | | | | |
|---|---|---|---|---|
| 3,675,357 A | * | 7/1972 | Magee | A01K 11/002 40/300 |
| 6,055,752 A | * | 5/2000 | Ritchey | A01K 11/002 40/301 |
| 7,441,354 B2 | * | 10/2008 | Ritchey | A01K 11/003 119/655 |
| 9,554,557 B2 | * | 1/2017 | Nehls | A01K 11/003 |
| 10,039,263 B2 | * | 8/2018 | Teychene | A01K 11/00 |
| 2008/0044313 A1 | * | 2/2008 | Caisley | A01K 11/003 422/400 |
| 2008/0227662 A1 | | 9/2008 | Stromberg et al. | |
| 2008/0228105 A1 | * | 9/2008 | Howell | A01K 11/003 600/567 |
| 2009/0326548 A1 | * | 12/2009 | Nehls | A01K 11/003 606/116 |

(Continued)

FOREIGN PATENT DOCUMENTS

| | | |
|---|---|---|
| DE | 102008034677 | 1/2010 |
| EP | 1723847 | 11/2006 |

(Continued)

OTHER PUBLICATIONS

PCTEP2015081247 International Search Report and Written Opinion dated Mar. 17, 2016, 16 pgs.

*Primary Examiner* — Sean P Dougherty

(57) ABSTRACT

The present specification relates to apparatus, methods and kits for applying an identification tag to an animal and removing a tissue sample from the animal. Apparatus of the disclosure cannot be manipulated to transfer an identification tag from one animal to another. An apparatus can comprise a sample container, a flap, a downholder clip and a cutting element that can be placed on a male part of an ear-tag and at least one element/feature that supports movement of the sample container out of the movement path of the male tag toward the female part of the ear-tag.

18 Claims, 31 Drawing Sheets

(56) References Cited

U.S. PATENT DOCUMENTS

| | | | | |
|---|---|---|---|---|
| 2010/0018469 A1* | 1/2010 | Gottschling | ......... | A01K 11/002 119/174 |
| 2010/0210011 A1* | 8/2010 | Hilpert | ................. | A01K 11/003 435/307.1 |
| 2011/0270267 A1* | 11/2011 | Ritchey | ................ | A01K 11/002 606/117 |
| 2013/0204159 A1* | 8/2013 | Destoumieux | ....... | A01K 11/003 600/564 |
| 2016/0235391 A1* | 8/2016 | Gardner | ............. | A61B 10/0266 |
| 2016/0249586 A1* | 9/2016 | Berner | ................ | A01K 11/003 600/567 |

FOREIGN PATENT DOCUMENTS

| | | |
|---|---|---|
| FR | 2929804 | 10/2009 |
| GB | 770785 | 3/1957 |
| WO | 2013060690 | 5/2013 |

* cited by examiner

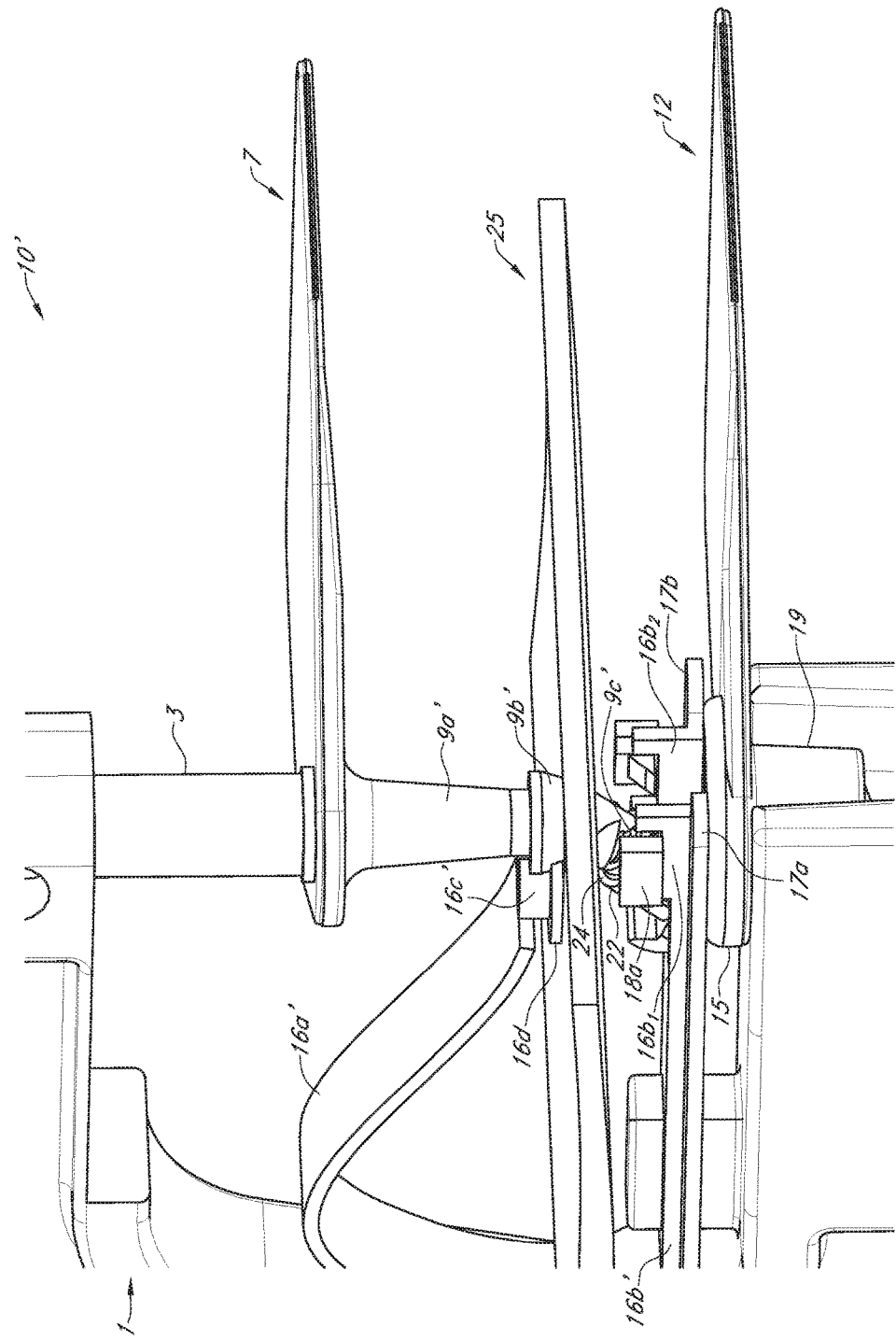

APPARATUS AND METHODS FOR TISSUE SAMPLING AND IDENTITY-TAG ATTACHMENT

CROSS-REFERENCE(S) TO RELATED APPLICATION

The present application claims priority under 35 U.S.C. § 119(e) to U.S. Provisional Patent Application Ser. No. 62/099,416, filed Jan. 2, 2015, the entire contents of which are incorporated herein by reference.

FIELD

The present specification relates to apparatus, methods and kits for sampling tissue and attaching an identification tag to an animal (e.g., an ear-tag). In some embodiments, apparatus, methods and kits described herein can be used for obtaining a tissue sample from an animal while attaching a tamper resistant identification tag to the animal.

BACKGROUND

Ear-tags are typically used for identifying animals such as production animals, livestock, farm animals, pets, and even some wild animals for research purposes. Ear-tags serve primarily to identify an animal and can be used for purposes such as but not limited to: organization and recording of livestock, to indicate the animal's owner, status of having a disease or being free of a disease, vaccination status, and traceability of livestock animals such as tracking movement of an animal through life including tracking its meat, meat processing or other animal product tracking. For example, in Europe an animal identity is printed on an official tag and is similar to a "passport ID of the animal".

Since procedures such as vaccination and/or testing an animal for a disease are expensive, attempted fraud procedures for misusing ear-tags is a possibility and has to be prevented. In particular, removing an ear-tag from one animal (such as a disease free and/or vaccinated animal) and transferring it onto another animal (such as an animal that has not been tested for a disease and/or not been vaccinated) has to be prevented.

Several ear-tags are presently available in the market. For example, U.S. Pat. No. 4,597,208 describes a two-part cattle ear-tag having male and female parts that interlock to attach to the ear and have a cap that protects the device from being removed and transferred from one animal to another. The cap is designed to be damaged by any attempt to manipulate the tag and the damaged cap is an indicator of tag-tampering.

Several laboratory tests are typically carried out on most farm and production animals to test the animals for having a disease, and/or being carriers of a disease, and/or for gene analysis for breeding purposes. Hence, there is a need to obtain samples of tissues from animals for laboratory testing. A tissue sample can conveniently be obtained from an animal during the application of an ear-tag for identification of the animal. An ear-tag applicator with a means to remove a part of ear tissue is described in US Patent Application 2010/0210011. The ear-tag described in this U.S. Patent application has a male and female part similar to that described in U.S. Pat. No. 4,597,208, but additionally comprises a cutting element in the male part and a sample holder in the female part for removing a sample of the ear tissue when piercing the ear. However, this device does not prevent tag-tampering since the sample holder container is located below the female part. Upon detachment of the sample container, the part below the female part of this ear-tag is freely accessible to a manipulator to transfer from one ear to another.

Accordingly, there is a need in the art for a better ear-tag attachment device that also provides for sample tissue isolation and furthermore prevents the ear-tag from being removed and transferred to another animal.

SUMMARY

The present specification relates in some embodiments to apparatus, methods and kits for applying an identification tag to an animal and removing a tissue sample from the animal. In some embodiments, the apparatus/device of the disclosure cannot be manipulated to transfer an identification tag from one animal to another.

In some embodiments, the disclosure describes a device for attaching an identity tag and removing a tissue sample comprising: an ear-tag applicator; a means to hold a sample container below a male part of the identity tag (male tag) and above a female part of the identity tag (female tag) and below the ear to which the identity tag is to be attached and from which tissue sample is to be removed; the male tag having a removable tissue cutting element; at least one holder reversibly connected to the removable tissue cutting element and/or a clamp reversibly connected to the sample container; the male tag having a movement path toward the female tag; and at least one part of the sample container or one part of the removable tissue cutting element having a feature that supports movement of the sample container out of the movement path of the male tag, wherein the sample container and the clamp remain in the movement path of the male tag when there is a connection between the holder and the removable tissue cutting element or when there is a connection between the clamp and the sample container or when both connections are there, wherein the connection between the holder and the removable tissue cutting element and/or the connection between the clamp and the sample container are released after a tissue sample is removed but before the male tag part enters the female part, and wherein when the connections (between the holder and the removable tissue cutting element and/or the connection between the clamp and the sample container) are released the sample container retains the removable tissue cutting element or at least a part thereof and the sample container moves out of the movement path of the male tag.

In some embodiments, the feature that supports movement of the sample container out of the movement path of the male tag is an asymmetric bottom of the sample container. In some embodiments, the feature that supports movement of the sample container out of the movement path of the male tag is a slit in the removable tissue cutting element. In some embodiments, the feature that supports movement of the sample container out of the movement path of the male tag is a hinge integrated in the removable cutting element. In some embodiments, the feature that supports movement of the sample container out of the movement path of the male tag is a part of the removable tissue cutting element wherein the removable tissue cutting element is made up of more than one parts.

In some embodiments, of a device of the disclosure, the at least one element that can cause the sample container to move out of the movement path of the male tag, following removal of the tissue sample and placement of cut tissue sample into the container and detachment of removable cutting element, is: an asymmetric bottom of the sample container, a tissue cutting element, a part of the tissue cutting element, a hinge integrated in the tissue cutting element, or any combination thereof.

An ear-tag applicator that can be used in a device of the disclosure is or can be a pliers, a modified pliers or a commercial ear-tag applicator. A modifies pliers in some embodiments can have one, more or all of the following modifications such as: 1) a base upon which is disposed a cavity, a space or a grove where the female part of an ear-tag can be removable placed or fit upon; 2) a base upon which is disposed a second cavity, space or a groove into which a downholder clip can be reversibly placed into; 3) a base having both features 1) and 2); 4) having at least two handles pivotable about an axial bore such that a pin attached to a guide bore connected to the axial bore can move up and down by movement of the handles; 5) the pin attached to the guide bore having a shape complementary to the interior of a male-par of an ear-tag such that the make part of ear-tag can fit onto the pin detachably.

In some embodiments, of a device of the disclosure, the means to hold the sample container below the male tag and above the female tag is a flap. In some embodiments, the flap further connects the sample container to the male tag. In some embodiments, the flap is further connected to the ear-tag applicator. In some embodiments, the at least one holder is a part of the flap.

In some embodiments, the flap is fabricated by selective laser-sintering. In some embodiments, the clamp and the sample container are fabricated by selective laser-sintering. In some embodiments the flap, the clamp and/or the sample container are comprised of PA12 powder. In some embodiments the PA12 powder also comprises glass balls. In some embodiments the flap can have a coefficient of elasticity of 1500 MPA.

In some embodiments of a device of the disclosure, the removable tissue cutting element or part thereof that is retained by the sample container after the connections are released forms a lid on the sample container. A lid so formed can form an airtight seal and prevents a tissue sample inside the sample container from being contaminated or degraded.

In some embodiments, the disclosure describes a device for attaching an identity tag and removing a tissue sample comprising: an ear-tag applicator; a sample container; a means to hold a male tag part of the identity tag onto portions of the ear-tag applicator; a means to hold a female tag part of the identity tag below the male tag and below the ear; a means to hold a sample container below both the ear and the male tag and above the female tag; the male tag having a tissue cutting element at least a part of which can detach from the male tag after excision of the ear tissue and attach to the sample container; and at least one element that can cause the sample container to move out of the path of movement the male tag, following removal of the tissue sample and placement of cut tissue sample into the container and detachment of tissue cutting element or a part thereof, such that the male tag can move toward and enter the female tag to fit together thereby attaching the ear-tag to the ear.

In some embodiments, the at least one element that can cause the sample container to move out of the movement path of the male tag, following removal of the tissue sample and placement of cut tissue sample into the container and detachment of removable cutting element, is: an asymmetric bottom of the sample container, the tissue cutting element, a part of the tissue cutting element, a hinge integrated in the tissue cutting element or any combination thereof.

In some embodiments, the means to hold a male tag part of the identity tag onto portions of the ear-tag applicator comprises: a flap; a pin on the ear-tag applicator; and optionally further comprises a downholder clip; and the means to hold the sample container below both the ear and the male tag and above the female tag comprises: the flap; a clamp; and optionally further comprises the downholder clip. As described in sections below portions of a flap, a clamp and a downholder clip can be used to hold various components.

In some embodiments, the means to hold the female tag part of the identity tag below the male tag and below the ear is a space, a cavity or a groove on the ear-tag applicator into which portions of the female tag part can reversibly fit into. In some embodiments, a means to hold the female tag comprises a space, cavity or a groove on the ear-tag applicator wherein at least a portion of the female part tag can reversibly fit into. In some embodiments, a means to hold the female tag comprises at least one of a space, a cavity, a groove, a clamp, a clip, a magnet, a magnetic force and any combinations thereof that can hold a female tag or part thereof onto or near an ear-tag applicator.

In some embodiments of the disclosure, the sample container comprises a chamber for storing excised tissue. A sample container can also additional contain a desiccant, a preservative, a buffer or any combinations thereof.

In some embodiments of a device of the disclosure, the tissue cutting element or part thereof which detach from the male tag after excision of the ear tissue can then attach to the sample container to form a lid on the sample container.

In some embodiments, a pin on the ear-tag applicator is movable up and down by movement of one or more plier handles about a pivotable axis on the ear-tag applicator. In some embodiments the pin on the ear-tag applicator has a part shaped to have a complementary fit with a structure in the male tag.

Some embodiments of the disclosure describe a device for attaching an identity tag and removing a tissue sample comprising: an ear-tag applicator; a sample container having an asymmetric shaped bottom part; means to hold a male tag part of an ear-tag onto portions of the ear-tag applicator that can move up and down to pierce an ear; means to hold a female tag part of an ear-tag directly below a male tag and ear such that the male tag portions can enter the female tag to fit together attaching the ear-tag to the ear; means to hold a sample container below both the ear and the male tag and above the female tag; and the male tag having a tissue cutting element and an element that can detach from male tag after excision of the ear tissue to form a lid on the sample container.

A flap, in some embodiments, is a part that is operable to reversibly hold one or more of the following including: 1) a male tag; 2) a sample container; and/or 3) one or more clamps, onto or near an ear-tag applicator.

A downholder clip, in some embodiments is a part operable to hold one or more components reversibly onto or near an ear-tag applicator including: 1) portions of a flap, 2) portions of a sample holder, and/or 3) one or more clamps.

The present disclosure in some embodiments describes a device for attaching an identity tag and removing a tissue sample comprising: 1) a flap that is operable to reversibly hold one or more of the following including: a) a male tag; b) a sample container; and/or c) one or more clamps, onto or near an ear-tag applicator; 2) a downholder clip operable to hold one or more components reversibly onto or near an ear-tag applicator including: a) portions of a flap, b) portions of a sample holder, and/or c) one or more clamps; a sample container; and one or more clamps.

In some embodiments, a device of the disclosure can further comprise an ear-tag applicator. In some embodiments, a device of the disclosure can further comprise an ear-tag comprising a male part and a female part.

In some embodiments, the sample container of a device of the disclosure can comprise an asymmetric bottom. In some embodiments, the tissue cutting element or a part of the tissue cutting element can be configured to have an element that can cause the sample container to move out of the way of the male tag after the ear is pierced and the tissue sample is placed into the sample container. In some embodiments, the element that can cause the sample container to move out of the way can be a hinge integrated in the tissue cutting element. In some embodiments, the element that can cause the sample container to move out of the way can be a slit on the tissue cutting element. In some embodiments, the element that can cause the sample container to move out of the way of a male tag can be a hinge or a slit in the tissue cutting element or a combination thereof.

A device of the disclosure, in some embodiments, further comprises means to enable working with a multi-well sample processor device. Samples of tissue obtained by a device of the disclosure in its sample container can be aligned with multi-well devices, such as 96-wells, 384-wells, 1536 wells and the like since sample containers of the disclosure have dimensions that allow them to align onto multi-well plates. For example, the asymmetric bottom part of sample containers of the disclosure disposes a cut-out or a cavity into which a protrusion of the next container (in a multi-well container configuration) can be aligned when aligned in a multi-well format, such as a 96-well format, a 384-well format, and/or a 1536 well format.

In some embodiments, the footprint of each sample container can be larger than a diameter of 9 mm and would fit into a multi-well format. Accordingly, devices of the disclosure can be used with a multi-well processing device for simultaneous sample tissue processing or testing after tissue extraction by moving sample containers of the disclosure onto multi-well plates.

In some embodiments the present disclosure provides a sample container designed for retaining tissue sample while an ear-tag is being applied and ear tissue is being removed while the ear-tag is applied. A sample container of the disclosure is designed for making removal of tissue and application of an ear-tag easier, efficient and/or time saving.

In some embodiments, the disclosure provides a sample container comprising: an asymmetric bottom part; dimensions configured to be smaller than a chamber of a female part of an ear-tag (female tag); a chamber designed to contain a tissue sample; a top part of the sample container configured to be able to fit a tissue cutting element or part thereof of a male tag part of an ear-tag (male tag), wherein the tissue cutting element or part thereof can detach from the male tag form a lid on the sample container; optionally, an area to store a tissue desiccant or a tissue preservative; wherein the asymmetric bottom shape is configured to allow movement of the sample container out of the movement path of the male tag after an ear tissue is cut and placed into said sample container, thereby allowing the male tag to move downward after it pierces through an ear to enter the chamber of the female tag and form a seal.

In some embodiments, a sample container of the disclosure further comprises elements to interact with a clamp. In some embodiments, a sample container of the disclosure further comprises elements to interact with a flap.

In some embodiments, a sample container of the disclosure is fabricated by selective laser-sintering. A sample container of the disclosure can comprise PA12 powder and can additionally comprise glass balls.

In some embodiments, a sample container of the disclosure has dimensions to fit into a single well of a multi-well device. For example, the asymmetric bottom part of sample containers of the disclosure disposes a cut-out or a cavity into which a protrusion of the next container (in a multi-well container configuration) can be aligned when aligned in a multi-well format, such as a 96-well format, a 384-well format, and/or a 1536 well format. In another example, the footprint of each sample container can be larger than a diameter of 9 mm and would fit into a multi-well format. A sample container according to the various embodiments can be used in devices of the disclosure to retain removed ear-tissues. A sample container of the disclosure can be used to process and/or test samples obtained in multi-well devices such as a 96-well device, a 384-well device or a 1536 well-device or similar multi-well devices.

In some embodiments, the disclosure describes methods of attaching an identity tag and removing a tissue sample comprising: reversibly attaching a male-part of an ear-tag (male tag) having a tissue cutting element onto an ear-tag applicator in a position above an ear to which the tag is to be attached and from which tissue sample is to be obtained from; placing a female part of an ear-tag (female tag) onto the ear-tag applicator such that the female tag is below the male tag; placing a sample container in position below the male tag and the ear and above the female tag; moving the male-part of the ear-tag by means of the ear-tag applicator downward toward and through the ear such that the tissue cutting element of the male tag pierces through the ear and places the excised ear tissue into the sample container, thereby obtaining ear-tissue sample in the sample container; causing the sample container to move transversely out of way of the descending male tag; continuing to move the male tag downward to the female tag; and forming a seal between the male tag and female tag parts, thereby attaching the ear-tag to the ear.

Methods of the disclosure can use any embodiment of devices as described in this application. In some embodiments, a method can use ear-tag applicator such as a pliers, a commercially available ear-tag applicator or a pliers adapted to attach ear-tags.

In some embodiments of a method of the disclosure, a female tag can be placed detachably in a groove, a cavity or a space of the ear-tag applicator fashioned to receive at least a part of the female tag.

In some embodiments of a method of the disclosure, a male tag is attached to the ear-tag-applicator by a pin on the ear-tag applicator. The pin is movable up and down by means of one or more plier handles about a pivotable axis. In some embodiments of a method of the disclosure, a male tag comprises a hollow stalk inside of which is an element designed to fit into the pin of the ear-tag applicator, the element having a complementary shaped region to fit into the pin.

In some embodiments of a method of the disclosure, the sample container is held in place prior to and during piercing of the ear tissue by means of a downholder clip, one or more clamps, a flap and any combinations thereof.

In some embodiments of a method of the disclosure, a sample container has an asymmetric shaped bottom which causes transverse movement of the sample container out of the movement path of the male tag after the ear tissue is cut and placed inside the sample container.

In some embodiments of a method of the disclosure, a hinge and/or a slit in a tissue cutting element can cause the sample container to move out of the movement path of a male tag.

In some embodiments of a method of the disclosure, an asymmetric shaped bottom of a sample container and/or a hinge and/or a slit in a tissue cutting element and any combination of the above can cause the sample container to move out of the movement path of a male tag.

In some embodiments of a method of the disclosure, further comprising a step of detaching a tissue cutting element or part thereof from a male tag to form a lid on the sample container after the excised ear tissue is placed into the sample container.

In some embodiments of a method of the disclosure, removing the ear tissue sample can comprise piercing the ear tissue, punching a hole in the ear tissue, cutting the ear tissue, tearing off the ear tissue or perforating the ear tissue.

Some other embodiments describe methods for attaching an identity tag and removing a tissue sample from an animal comprising: reversibly attaching a male-part of an ear-tag (male tag) having a tissue cutting element onto an ear-tag applicator in a position above an ear that is to be tagged and from which sample is to be obtained; placing a female part of an ear-tag (female tag) onto or near the ear-tag applicator; placing a sample container having an asymmetrical bottom part in position below the male tag and the ear and above the female tag; moving the male-part of the ear-tag by means of the ear-tag applicator downward toward and through the ear such that the tissue cutting element of the male tag pierces through the ear and places the excised ear tissue into the sample container; continuing to move the male tag downward to the female tag past the sample container such that movement of the male tag moves the sample container transversely out of way of the descending male tag; and forming an attachment between the male tag and female tag, thereby attaching the ear-tag to the ear and obtaining ear-tissue sample in the sample container.

In some embodiments of a method of the disclosure an ear-tag applicator is a pliers, a commercially available ear-tag applicator or a pliers modified or adapted as described herein to attach ear-tags and obtain samples. In some embodiments of a method of the disclosure, a female part of the ear-tag is placed in a groove, a cavity or a space on the ear-tag applicator fashioned to receive the female part container. In some embodiments of a method of the disclosure, a female tag is placed near or onto an ear-tag-applicator by means of one or more of clamps, clips, magnets and/or magnetic forces.

In some embodiments of a method of the disclosure, a male tag is attached to the ear-tag-applicator by a pin on the ear-tag applicator that is movable up and down by means of one or more plier handles up and down a pivotable axis. In some embodiments of a method of the disclosure, a the male tag comprises a hollow stalk inside of which is a complementary shaped element designed to fit into the pin of the ear-tag applicator and the male tag is attached to the pin by fitting the complementary shapes on the pin and the interior of the male tag into each other.

In some embodiments of a method of the disclosure, a sample container is held in place prior to and during piercing of the ear tissue by means of one or more of a downholder clip, one or more clamps and/or a flap. In some embodiments of a method of the disclosure, the asymmetric shape of the sample container at the bottom facilitates the transverse movement of the sample container following movement of the male tag components toward the female tag located directly below the original place of the sample container.

A method of the disclosure can further comprise detaching part of male tag to form a lid which is placed on the sample container after the excised ear tissue is placed in. In some embodiments, part of the male tag that detaches to form a lid is a punch or a tissue cutting element thereof.

The present disclosure, in some embodiments, describes kits for attaching an ear-tag and excising tissue. A kit of the disclosure can comprise a flap operable to reversibly hold: a male tag on an ear-tag applicator, a sample holder, and one or more clamps; a downholder clip operable to reversibly hold one or more portions of the flap; a sample container having an asymmetrical base; and one or more clamps.

In some embodiments, a kit of a disclosure can further comprise one or more components including: an ear-tag applicator; and an ear-tag comprising male tag components and female tag components. Both these parts are commercially available and one or more of these parts can be modified as described in this specification.

In some embodiments, a kit can have a sample container that is pre-packaged with a desiccant material, a preservative, and/or a buffer inside it. Instructions manuals can be part of a kit of the disclosure.

Some embodiments of the present disclosure can provide one or more technical advantages. Exemplary technical advantages of some embodiments include one or more of the following: superior tamper-evidence characteristics; prevention of tampering of ear-tags; more robust alignment of container above female tag blind hole allows larger tissue cutting force; design that ensures container does not move till tissue is extracted; works with any ear-tag & any ear-tag applicator on market; enables comfortable handling in the field and lab; and/or a design that enables alignment in a 96 well plate interface.

One or more advantageous features of the device or method or kit of the disclosure, in some embodiments, comprise: 1) asymmetric shape of sample container at the base that allows for transverse movement of sample container out of way of the male tag following sample removal; 2) location of sample container being directly below the male tag and directly above the container of the female tag into which the male tag parts enter for attachment to ear; 3) clamp mechanism between sample container and ear-tag which allow sample container to be released when needed and in-place when needed; 4) flap to hold male part of ear-tag in place in relation to the ear-tag applicator; and 5) tamper-proof ear-tag application while simultaneously obtaining a tissue sample for analysis reduce the time and money needed for such procedures.

While specific advantages have been disclosed hereinabove, it will be understood that various embodiments may include all, some, or none of the previously disclosed advantages. Other technical advantages may become readily apparent to those skilled in the art in light of the teachings of the present disclosure.

These and other features of the present teachings will become more apparent from the detailed description in sections below.

BRIEF DESCRIPTION OF THE DRAWINGS

One or more embodiments of the present disclosure may be better understood in reference to one or more the drawings below. The skilled artisan will understand that the drawings, described below, are for illustration purposes only. The drawings are not intended to limit the scope of the present teachings in any way.

FIG. 17A depicts transverse movement of sample container with tissue sample and the male part of the ear-tag traveling through the slit of the cutting element following ear piercing during use of the device of FIG. 14A, according to one embodiment of the disclosure;

DETAILED DESCRIPTION

Figure 1:
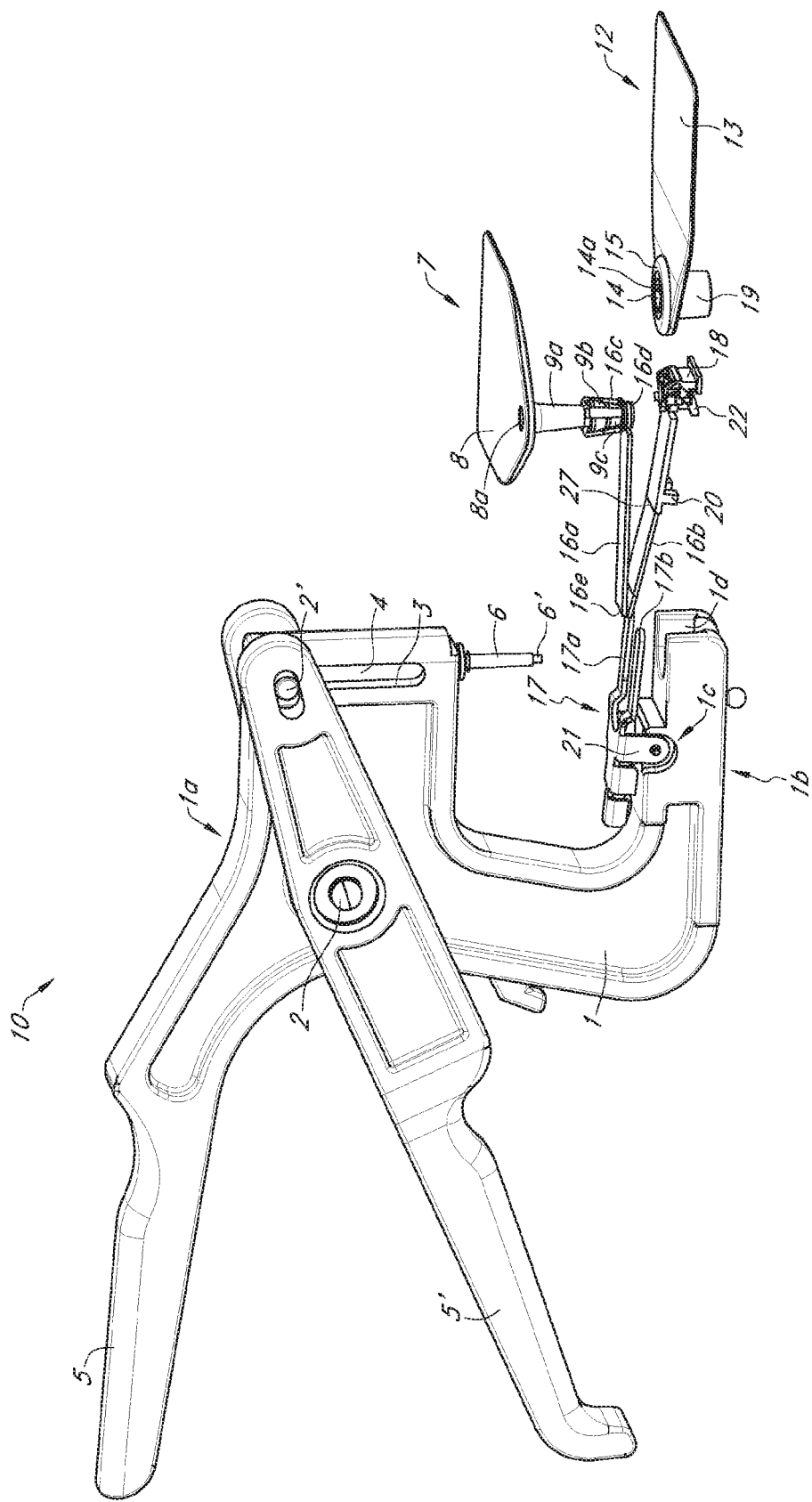
FIG. 1 depicts a side view of an identification tag applicator device having a sample withdrawal component and a sample retainer container and depicts in addition components such as pliers, male and female parts of an ear-tag, downholder clip and clamping elements, according to one embodiment of the disclosure.

It is to be understood that both the foregoing general description and the following detailed description are exemplary and explanatory only and are not intended to limit the scope of the current teachings. In this application, the use of the singular includes the plural unless specifically stated otherwise. Also, the use of "comprise", "contain", and "include", or modifications of those root words, for example but not limited to, "comprises", "contained", and "including", are not intended to be limiting. Use of "or" means "and/or" unless stated otherwise. The term "and/or" means that the terms before and after can be taken together or separately. For illustration purposes, but not as a limitation, "X and/or Y" can mean "X" or "Y" or "X and Y".

Whenever a range of values is provided herein, the range is meant to include the starting value and the ending value and any value or value range there between unless otherwise specifically stated. For example, "from 0.2 to 0.5" means 0.2, 0.3, 0.4, 0.5; ranges there between such as 0.2-0.3, 0.3-0.4, 0.2-0.4; increments there between such as 0.25, 0.35, 0.225, 0.335, 0.49; increment ranges there between such as 0.26-0.39; and the like.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

The section headings used herein are for organizational purposes only and are not to be construed as limiting the subject matter described in any way. All literature and similar materials cited in this application including, but not limited to, patents, patent applications, articles, books, treatises, and internet web pages, regardless of the format of such literature and similar materials, are expressly incorporated by reference in their entirety for any purpose. In the event that one or more of the incorporated literature and similar materials defines or uses a term in such a way that it contradicts that term's definition in this application, this application controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

The specification, in some embodiments, describes an apparatus or device for attaching or affixing an identification tag to an animal. In some embodiments, an identification tag of the present disclosure is an ear-tag. An apparatus of the disclosure, in some embodiments, comprises an ear-tag applicator device. In some embodiments, an apparatus for attaching an identification tag of the disclosure further comprises a tissue sample remover (also referred to variously herein as cutting element, punch, tissue cutter, tissue cutting element) to extract a tissue sample from an animal that the identity tag is being affixed/attached to.

An apparatus can comprise a sample container, a flap, a downholder clip and a cutting element that can be placed on a male part of an ear-tag and at least one element/feature that supports movement of the sample container out of the movement path of the male tag toward the female part of the ear-tag.

Removal or extraction of a tissue can comprise excising a part of tissue, and/or cutting a part of tissue, and/or forming a perforation in a tissue and/or punching out a tissue thereby obtaining part of tissue for use as a sample. Extracted tissue can then be stored and/or subject to sample processing as and when needed. Exemplary tissue types that can be extracted by devices and methods of the disclosure are, but are not limited to, skin, cartilage, blood, muscle, ear tissue, and the like.

In some embodiments, an identification tag applied using a device of the present disclosure, cannot be tampered and removed and/or moved from one animal to another.

In some embodiments, apparatus for identity-tag attachment and sample removal of the present disclosure comprise a sample holder component and a sample extracting component designed to interact with a tissue sample, such that a transversely directed movement path is created for the excised/cut tissue sample after it is placed in the sample holder. The sample extracting component has a tissue cutting element and a male part of the identity tag. According to these embodiments, a movement of the sample holder is produced which removes the sample (contained in the sample holder) sideways out of the movement path of the sample extracting components male tag component. Consequently the male tag part attaches to a female part of the identity tag (which is positioned below the sample extracting component), thereby attaching the identity tag to the tissue that now has a perforation/cut portion created by the removal of sample tissue. The tissue cutting element or parts thereof form a lid on the sample holder after tissue cutting and placement of the cut tissue into the sample holder and prior to movement of the now sealed (with lid) sample holder. Identity tag attachment is accomplished without the sample holder component being in the way of the identity tag. Identity tags attached by the apparatus of the present disclosure, allow for use of conventional techniques and/or parts for prevention of manipulation of an attached identity tag, such as but not limited to, cover caps to cover the front and back parts of an identity tag.

In some embodiments, an identity tag of the disclosure is an ear-tag. Apparatus of the present disclosure are able to use any ear-tags, including ear-tags that are available in the market, and attach such ear-tags and to obtain sample tissue from any ear such a tag is attached to. These include ear-tags which have been used for a long time and are officially approved. Apparatus of the disclosure is not limited to use of any particular ear-tag. Accordingly, devices of the disclosure enable sample removal while attaching an ear-tag whilst maintaining a high level of protection against manipulation.

Drawings provided herein can be used to understand embodiments of the present disclosure. While the drawings provide a guide to understand exemplary embodiments, the drawings are not to be construed as limiting the teachings of this disclosure. Part numbers used in the drawings are same or similar in function unless expressly described as otherwise.

FIG. 1 depicts a schematic side view of an exemplary apparatus 10 of the disclosure which is operable to apply an identity-tag and remove sample tissue, according to one embodiment of the disclosure. Apparatus 10 comprises pliers 1 (also called ear-tag applicator herein), ear-tag components comprising male-part of an ear-tag 7 and female part of the ear-tag 12, flap components 16 (16a, 16b, 16c, 16d . . . and the like), downholder clip 17 (17a, 17b . . . and the like), sample container 22, clamping elements 18 (18a, 18b . . . and the like).

Pliers 1, in some embodiments, comprise two handles 5 and 5' which are mounted so as be pivotable toward one another about an axial bore 2. Pliers 1 in some embodiments, comprise a bolt 4 which bears a pin 6 having a pin tip 6' at its bottom end. Bolt 4 is displaceably mounted in a guide bore 3, and bolt 4 moves when plier 1 handles are moved. Bolt 4 is permanently connected to bolt 2'. Bolt 2 is fixed to bolt 4 (e.g., by a press fit). Bolt 2' is moved by handle 5' inside guide bore 3. Bolt 4 is connected to handles 5 and 5' of pliers 1 by part 2' such that pivoting the two handles 5 and 5' of pliers 1 in a pliers-like manner moves pin 6 up and down during use of a device 10 (or 10') of the disclosure to apply an identity-tag and remove sample tissue.

In some embodiments, pliers 1 comprises pin 6 having a pin tip 6'. Pin tip 6' comprises a bottom end that can complementary fit with the inside of male ear-tag shank 9 (comprising parts such as 9a, 9b, 9c, . . . and the like). Top-end 1a of pliers 1 has handles 5 and 5' and bolt 4. In some embodiments, bottom-end of pliers 1b is a base in which is disposed grove 1c (also called cavity or space) which serves as a grove wherein downholder clip 17 is attached thereon by means of a connector 21. In some embodiments, bottom-end or base 1b also has another grove 1d wherein one or more components such as sample holder 22, clamping mechanism 18 and/or parts of female ear-tag 12, such as but not limited to parts 19 and 15 can be removably placed and/or moved therein.

In some embodiments, pliers 1, is an identity-tag applicator, such as for example an ear-tag applicator. In some embodiments, pliers 1 can be any ear-tag applicator device including any ear-tag applicators available in the market. One of skill in the art in light of the teachings provided herein, will realize that an apparatus according to the current disclosure, is not limited to pliers 1 as described in FIG. 1 or as described in any other drawings herein and any pliers can be modified for use with apparatus of the present disclosure.

Removably attached to pliers 1 is a downholder clip 17 (also called as clip 17). Downholder clip 17 is removably attachable to pliers 1 by connector 21, which could be a screw, a bolt, a connector, a roll pin, clamping pin or any connector element. In some embodiments, downholder clip 17 serves to hold down one or more of the following sample holder 22, clamping parts 18, female tag 12, flap components 16 and/or male-tag 7, either directly or via flap components 16. In some embodiments downholder clip 17 has additional parts that can be securely attached to the base of pliers 1 as depicted in FIG. 1 (but not expressly described as part numbers).

As depicted in the exemplary embodiment of FIG. 1, downholder clip 17 comprises two prongs 17a and 17b, which serve as guides to move flap 16, sample container 22, clamps 18, and male and female ear-tag components 7 and 12 respectively, in place while applying an ear-tag to an ear and withdrawing tissue therefrom. Other forms of guides are also contemplated. Various attachment devices can be used to attach and in some embodiments reversibly attach downholder clip 17 with flap 16. In some embodiments, downholder clip 17 can be made of materials such as, but not limited to, metals such as stainless steel, spring steel, coated steel or a rigid plastic.

Flap 16 can comprise various components such as but not limited to arms 16a and 16b. 16a and 16b can have various shapes (for example, also see the description of FIGS. 14A-17B). As depicted in the exemplary embodiment of FIG. 1, flap 16 has two arms 16a and 16b in a A-, V- and/or U-shaped configuration relative to each other and stacked one above another. As shown in FIG. 1, the area where arms 16a and 16b join, joint 16e, can be reversibly attached to end of downholder clip 17a or 17b. Joint 16e, during use of the device, can also be reversibly attached to portions of pliers 1 (see for example FIG. 2A). Attachment of flap 16 by joint 16e to pliers 1 can be achieved by several means including by magnetic means, double sided adhesive tape, a snap fit connection, a clip attached to the applicator. In some embodiments, the preferable attachment of 16 to 17 is by part 20 (FIGS. 1-13) or by part 28 (FIGS. 14A-17B).

In one embodiment, lower arm 16b can be slidably moved along or over downholder clip 17. Arms 16a and 16b can comprise one or more joints 27 along the length (for example see one joint 27 near part 20 on lower arm 16b). Joints 27 can be tilted up or down. Lower arm 16b holds sample container 22 at its distal end which is a container wherein cut/punched ear tissue will be held/retained. Sample container/holder 22 is held in place on flap 16 by means of a clamp 18. In some embodiments, part 16b' of flap 16 (shown for example in FIG. 4) can interact with portions of clamp 18 and sample container 22. Clamp 18 can comprise one or more clamps that are operable to clamp sample holder 22 in place during sample extraction and sample collection. Clamp 18 can be released to allow sample holder 22 to move transversely out of the way of male ear-tag 7 following sample extraction and sample collection.

In one embodiment, upper arm 16a has an extension (comprising for example, but not limited to, parts 16c and 16d) that can reversibly hold lower end of male ear-tag 7. As depicted in the example device of FIG. 1, upper arm 16a has a plurality of holders 16c. Holders 16c comprise upward extensions and can optionally have a top hook portion. Holders 16c are operable to hold onto parts of 9a or on part 9b of male ear-tag 7. In some embodiments, arm 16a can have at least 2, 3, 4, 5, 6, 7, 8 or more holders 16c. In some embodiments, arm 16a also comprises part 16d that forms a covering around the circumference of male ear-tag part 9c.

In some embodiments, parts 16 can be made of rigid or flexible plastics or metal sheets.

Figure 2A:
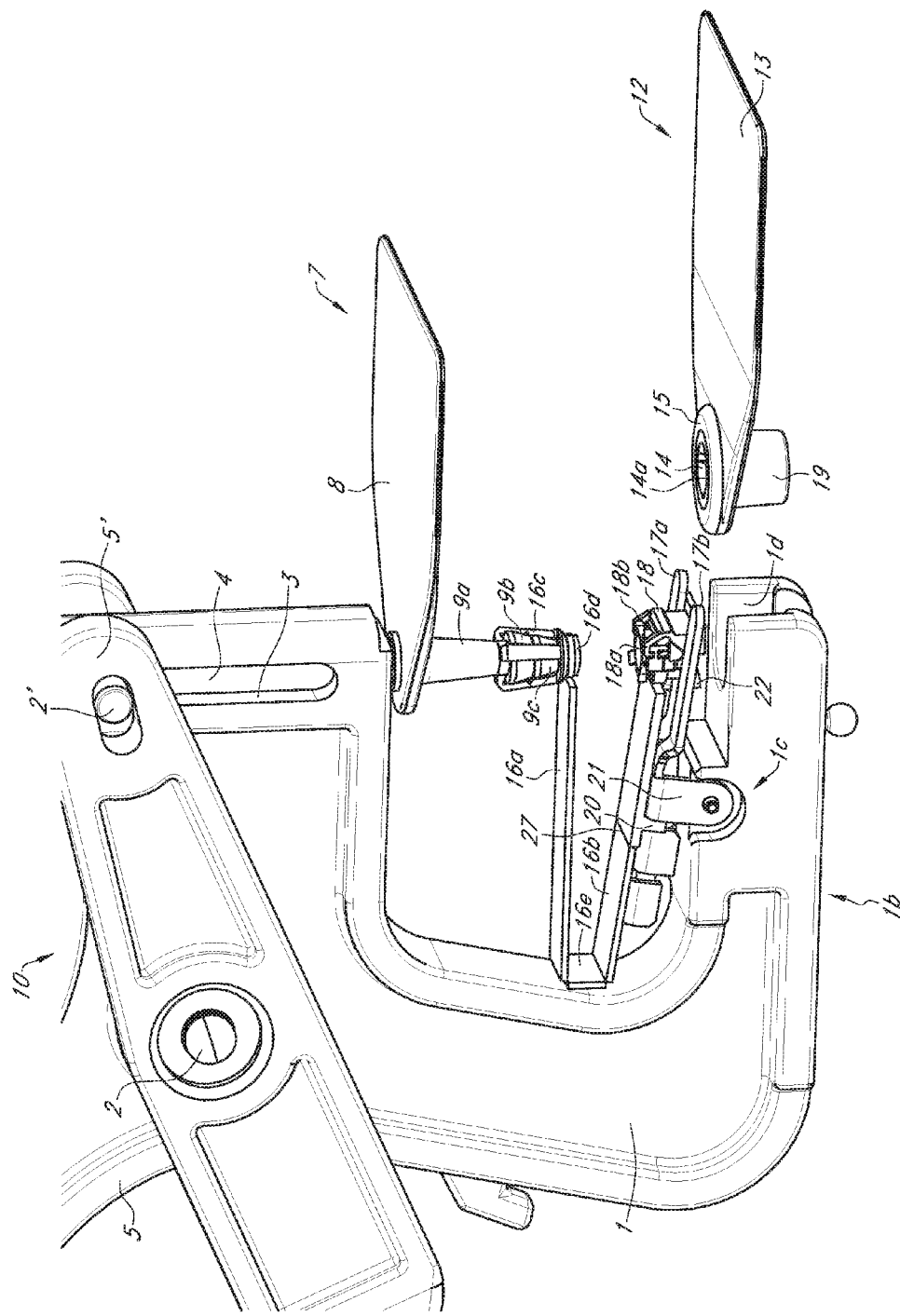
FIG. 2A depicts a side view of part of device of FIG. 1 showing a close-up view of male and female ear-tag parts, association of male ear-tag part with the pliers, flap and downholder clip, according to one embodiment of the disclosure.
Figure 2B:
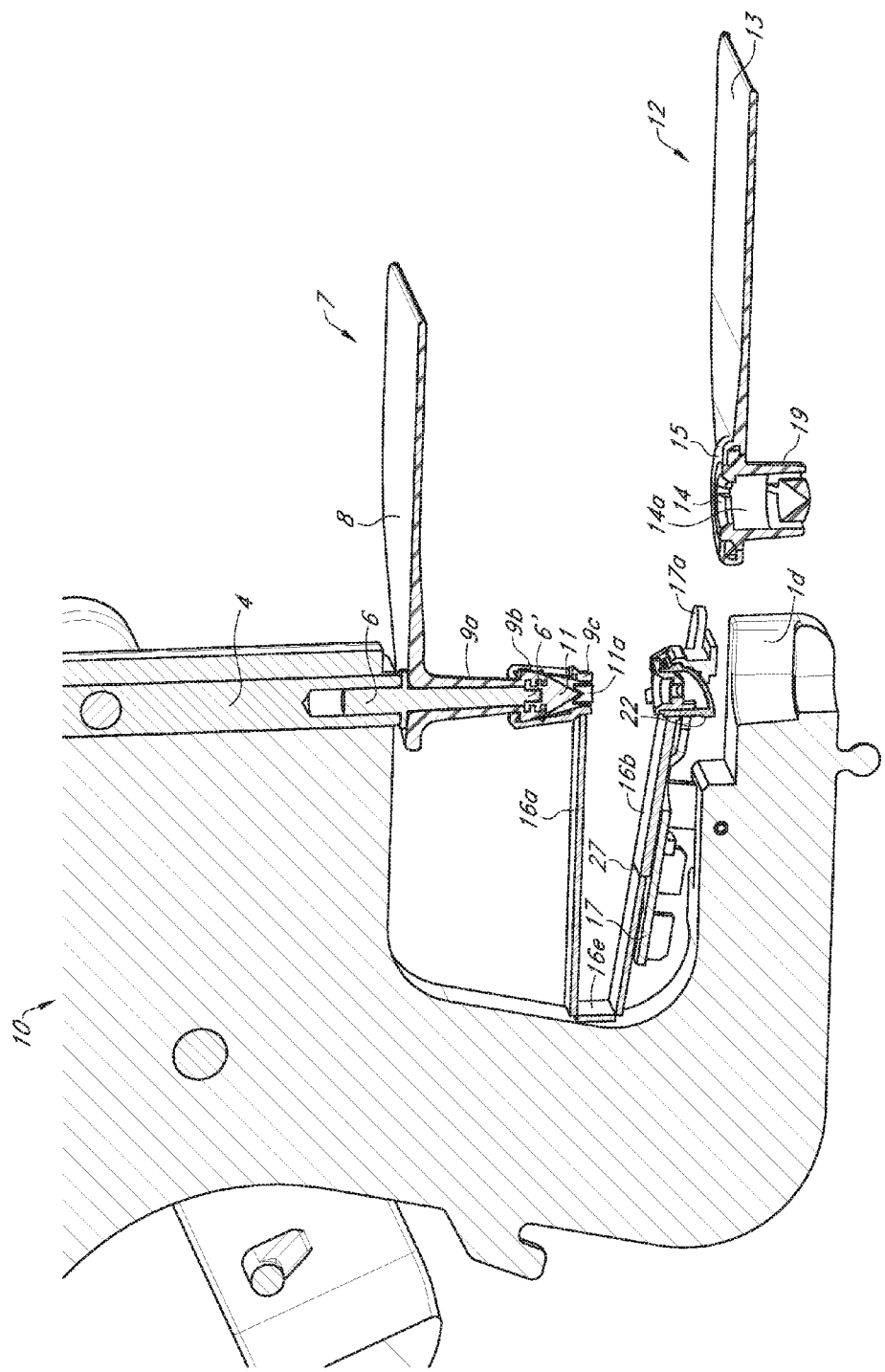
FIG. 2B depicts a cross-sectional view of the device of FIG. 2A.

In some embodiments, sample container 22 is an asymmetric shaped container having a cylindrical top portion and an asymmetrically curved bottom portion (see cross-section of container 22 in FIG. 2B). Sample container 22 in use of the device is designed to be place directly above female ear-tag chamber 14a prior to and during ear piercing (described below). The asymmetric shape of the bottom part of sample container 22, allows for transverse movement of container 22 out of the way of descending male tag part 11 following ear-tissue removal such that sample container 22 with part of cut tissue is no longer directly above container 14a allowing male-tag conical part 11 enter female tag to form a complementary fit and secure ear-tag onto ear.

FIG. 1 also depicts male-part of ear-tag 7 (also called male-tag or male ear-tag) comprising plate 8 and hole 8a from which shank 9 extends downward. In the embodiment shown in FIG. 1, shank 9 comprises sub-parts 9a, 9b and 9c. Internally, shank 9 has a conically formed part 11 and cutting element 11a (not expressly shown in FIG. 1, but shown in FIG. 2B). Shank 9 is hollow and operable to receive pin 6 having pin tip 6' (as shown in FIG. 2A).

While in use, male ear-tag 7 is placed on pin tip 6' (as shown in FIG. 2A). Shank 9 comprises stalk 9a toward the top and joining plate 8 at hole 8a, part 9b having a larger diameter than stalk 9a, and part 9c which comprises a tissue cutting element 11 and 11a (not expressly shown in FIG. 1, but see for example FIG. 2B). Tissue cutting elements 9c (comprising parts such as 11 and 11a) are also referred to as punch and/or tissue cutter and/or cutting element. In some embodiments, shank 9 is operable to be reversibly hooked in place by holder 16c.

FIG. 1 also depicts a female-part of ear-tag 12 (also called female-tag or female ear-tag) which comprises a perforated plate 13 and hole 14. Hole 14 has a lip 15 around it and immediately below hole 14 is chamber 14a. Chamber 14a is closed in an ear-tag manipulation-secure manner by a housing 19 which surrounds chamber 14a.

Housing 19 provides tamper resistance. If the two ear-tag parts (male and female) were to be separated, such as by application of a tensile force, shaft 9 will break. When shaft 9 is broken, male tag par 7 will not be reusable. Further, as part 9b will stay in housing 19, female tag 12 also cannot be reused as no new male tag part 9b can be introduced in the housing 19 as this space is still occupied by the broken part 9b of the first male tag.

A second aspect of tamper-evidence of housing 19 is, that (if the housing is rigid enough) no direct compressive force can be applied on 9b and 9b cannot be pushed out of housing 19 when one would try to separate the two ear-tag parts by a compressive force to avoid breakage of the part 9.

Chamber 14a is wider in diameter than the diameter of hole 14 such that the cutting element 9c of male tag 7, after penetrating the hole 14, is able to latch in due to lip 15 behind the edge of hole 14a. Consequently, when the identity-tag is attached, male part 7 and female part 12 of the ear-tag are secured in relation to one another.

In use, female-tag container 14a and hole 14 are disposed directly below sample container 22 and clamping elements 18.

FIG. 2A depicts a side view of part of device 10 of FIG. 1 and shows device 10 positioned with male ear-tag 7 attached to pliers 1 via pin 6 and sample container 22 is located directly below male ear-tag 7. Flap 16 is slidably moved on downholder clip 17 toward pliers 1 and joint 16e is attached to pliers 1. Part 20, which can be described as an "arm" or a "protrusion" or "arm of a snap-fit" on lower arm 16b of flap 16 can clip or fit into a corresponding grove on part 17 to align sample container 22 in position directly below male-tag 7. In use, when arm 16b slides over downholder clip 17 and reversibly attaches to pliers 1, male tag 7 is moved under pin 6. Pin 6 can be inserted into the opening 8a on male ear-tag 7 by movement of the plier handles 5 and 5' which move bolt 4 down. Alternatively, male tag 7 can be manually inserted onto pin 6.

FIG. 2B depicts a cross-sectional view of device 10 as depicted in FIG. 2A. Internal view of shank 9 depicts conical structure 11 and cutting element 11a located at the bottom of shank 9 in parts 9b 9c. Top of conical structure 11 fits into pin tip 6' of pliers 1. Cross section of female-tag 12 depicts internal container 14a surrounded by housing 19.

Figure 3:
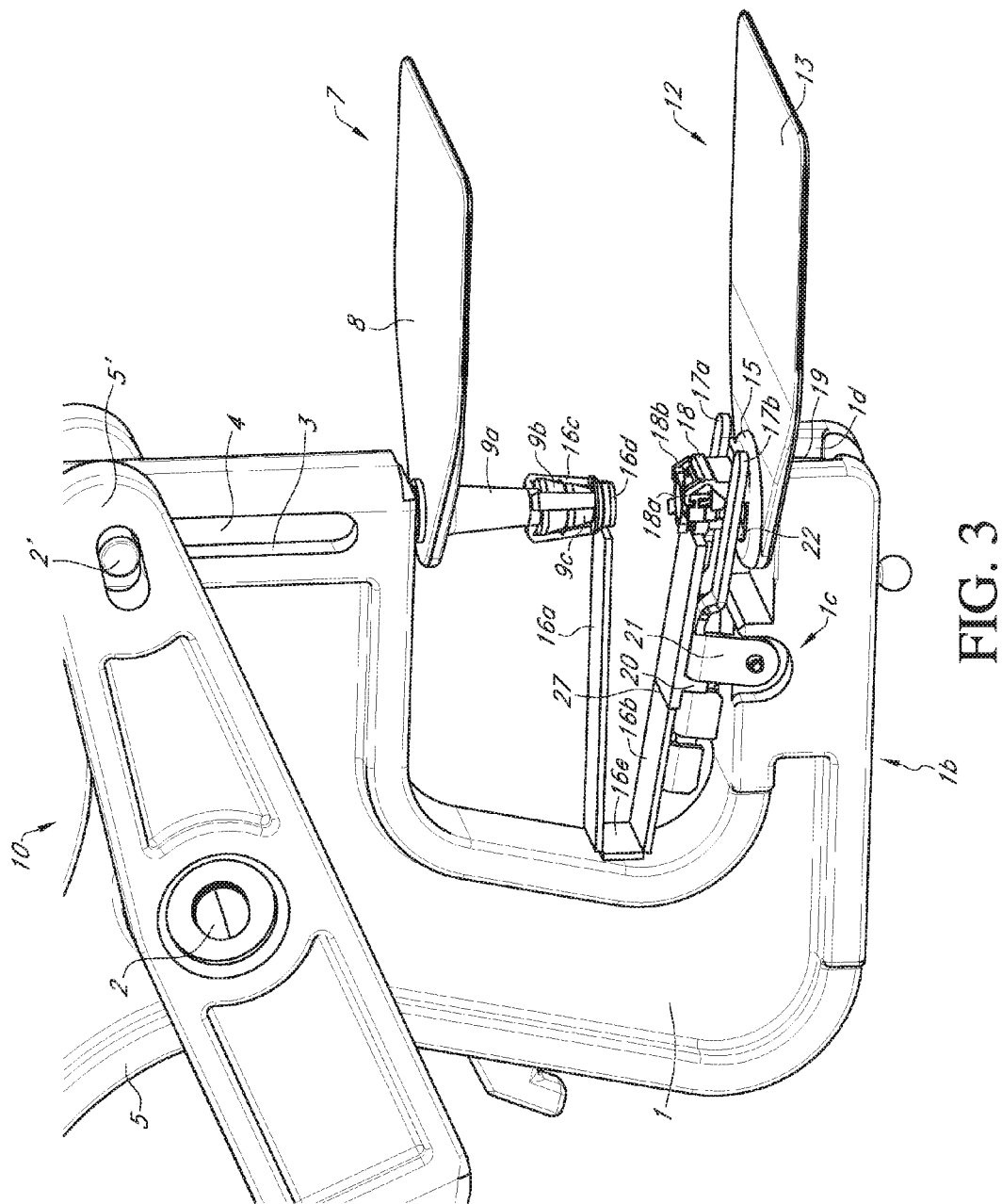
FIG. 3 depicts a side view of the device of FIG. 1 showing association of both male and female ear-tag parts with the pliers, flap, downholder clip and clamps, according to one embodiment of the disclosure.

FIG. 3 depicts a side view of device 10 showing association of female ear-tag 12 with the device. FIG. 3 depicts association of both male and female ear-tag parts with pliers 1, flap 16, downholder clip 17 and clamps 18. Chamber 14a of female ear-tag 12 is now positioned in grove 1d of pliers 1 and is located immediately below sample chamber 22 and clamp 18 and housing 19 of chamber 14a is visible in this figure. Female-tag 12 can be positioned manually.

Figure 4:
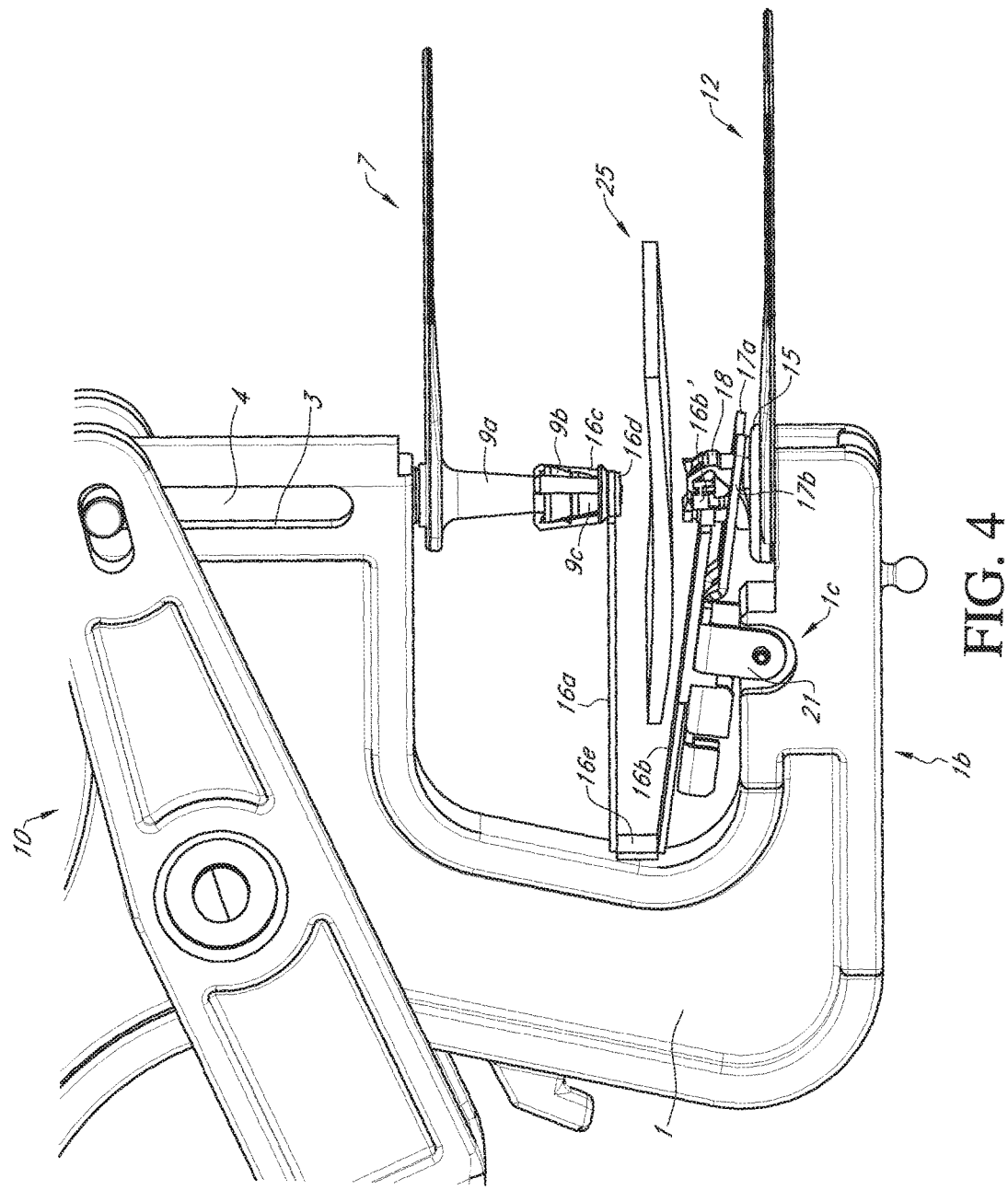
FIG. 4 depicts the location of an ear, to which the ear-tag is to be attached and from which sample tissue is to be removed, in relation to the device of FIG. 3, according to one embodiment of the disclosure.

FIG. 4 depicts an ear 25, to which an ear-tag is to be attached to and from which sample tissue is to be removed using a device of the disclosure, such as device 10 according to one embodiment. Part 16b' shown here is an extension of flap 16 arm 16b and holds sample container 22 in place. All other parts are as described in previous figures.

Figure 5:
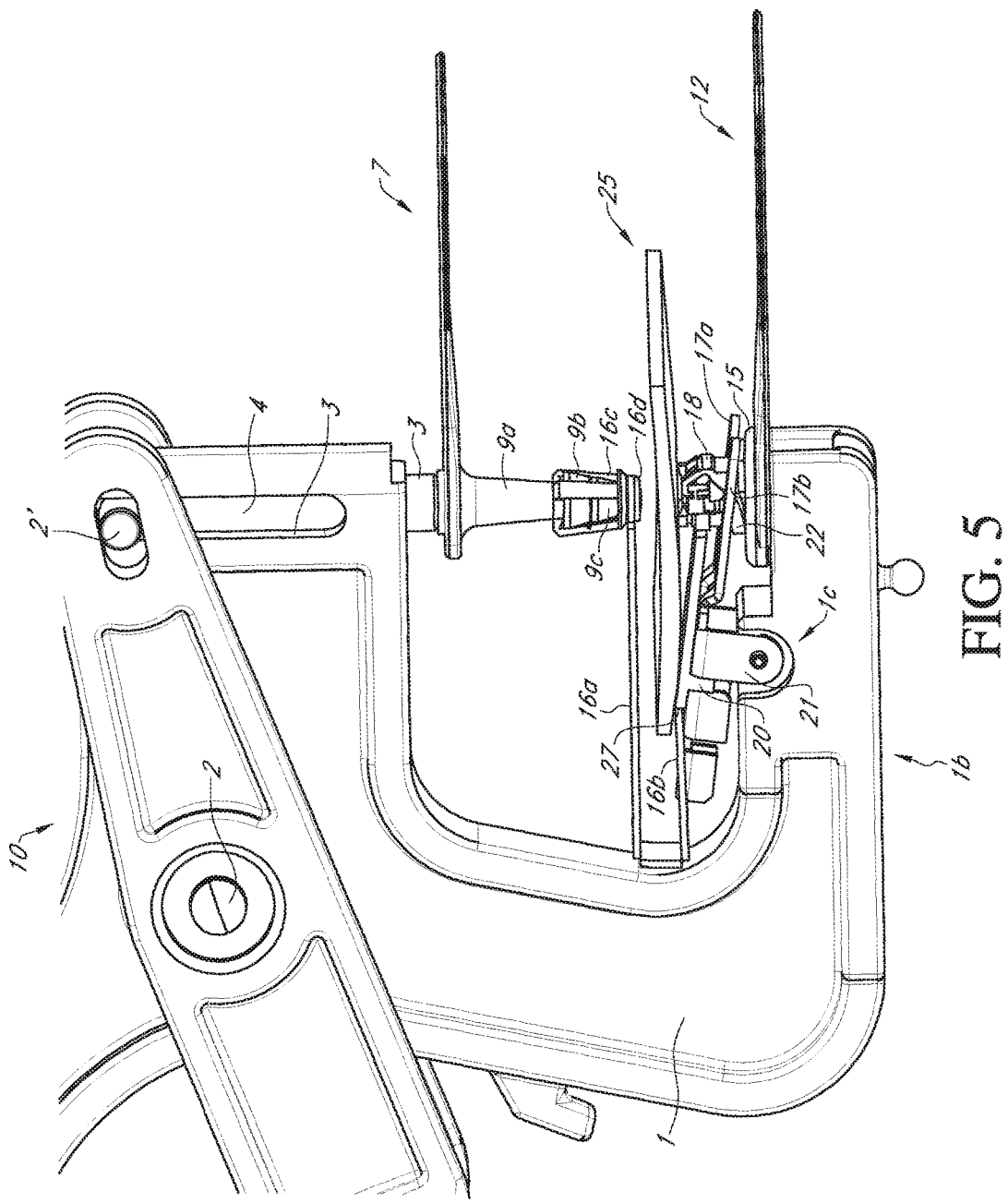
FIG. 5 depicts positioning of an ear, to which the ear-tag is to be attached and from which sample tissue is to be removed, on the device of FIG. 3, according to one embodiment of the disclosure.

FIG. 5 depicts positioning of ear 25, to which ear-tag (comprising male and female tag-parts 7 and 12 respectively) is to be attached and from which sample tissue is to be removed, on device 10, according to one embodiment of the disclosure. As shown herein, handles 5 and 5' of pliers 1 are rotated such that bolt 4 descends downward moving the proximal part of arm 16b parallel to arm 16a and moving a joint 27 on 16b upward, thereby tilting slightly downward distal part of 16b' and allowing ear 25 to be almost parallel to arm 16a.

Figure 6:
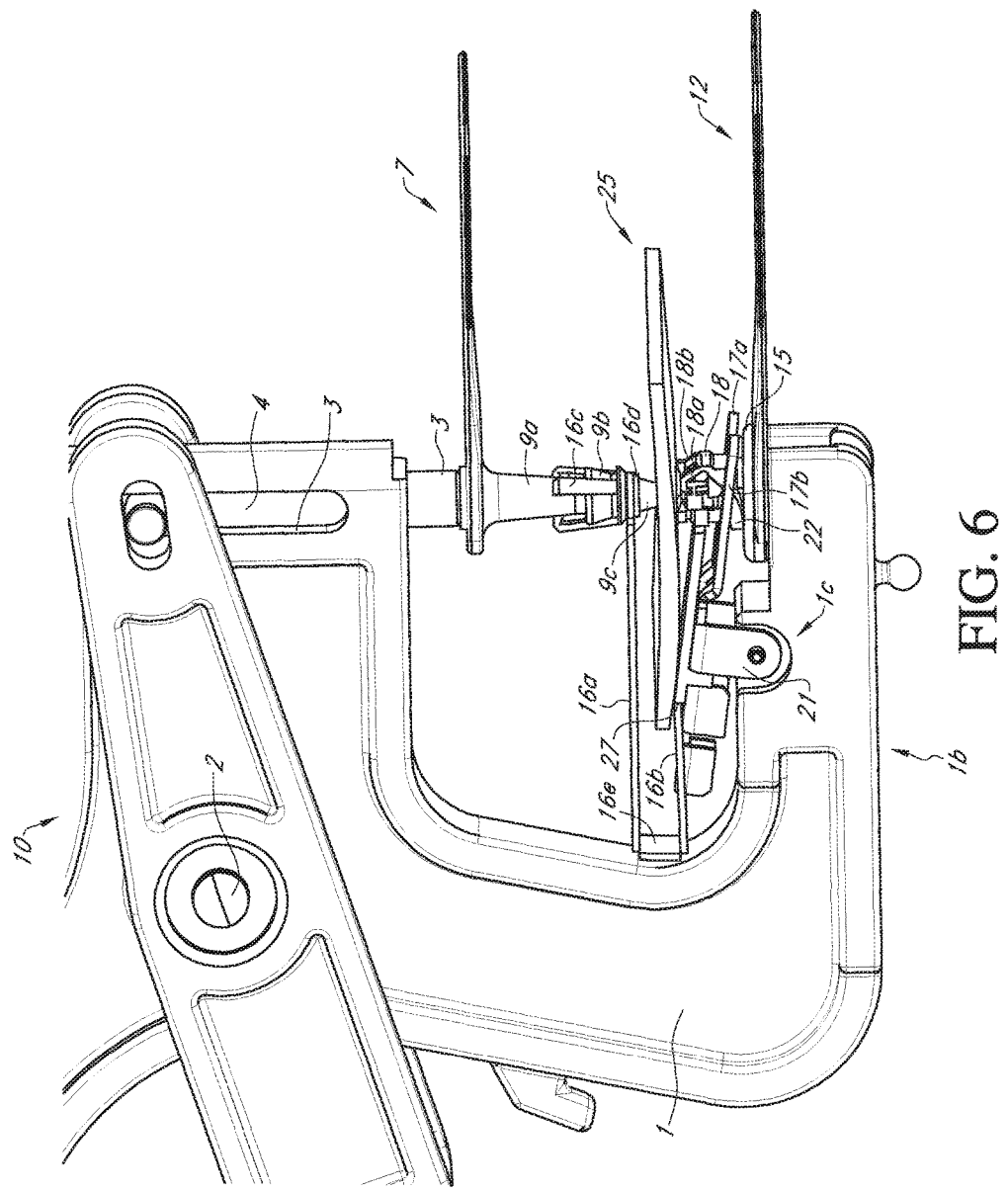
FIG. 6 depicts cutting component of the device of FIG. 3 starting to pierce ear 25, according to one embodiment of the disclosure.

FIG. 6 depicts cutting component 9c of device 10 starting to pierce ear 25, according to one embodiment of the disclosure. Bolt 4 descends further down to push down the cutting element 9c into ear 25 to begin cutting. Extensions of arm 16c are shown holding punch 9c before and during the ear-piercing. In addition, clamps 18a and 18b are shown holding sample container 22 in place during the cutting.

Figure 7A:
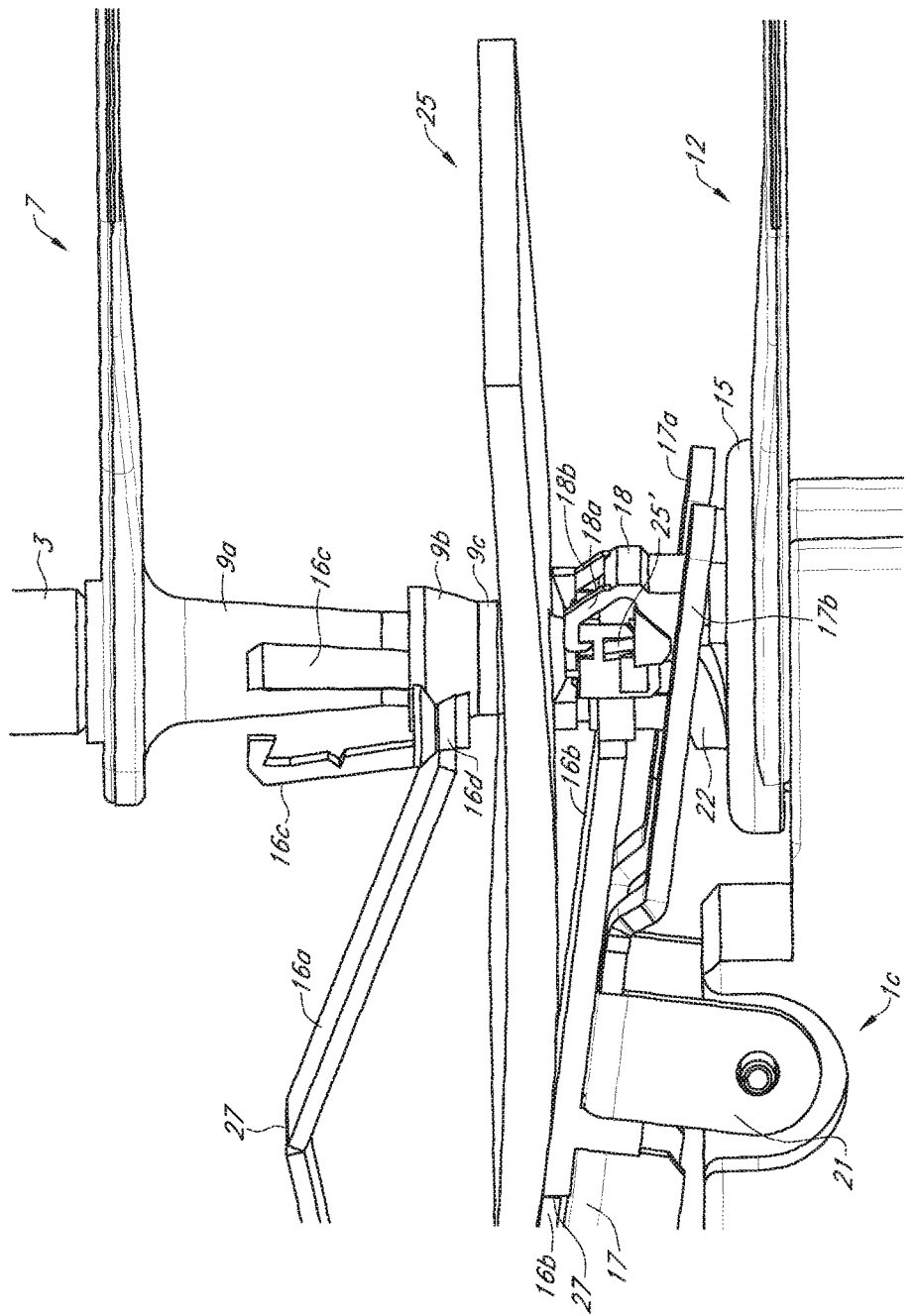
FIG. 7A depicts sample container with ear sample and position of cutting component and other parts of the device of FIG. 3 following piercing the ear, according to one embodiment of the disclosure.

FIG. 7A depicts a close-up view of part of device 10, showing sample container 22 containing ear sample 25' (not expressly visible in this view, see FIG. 7B) and showing the position of cutting component 9c and other parts of the device 10, following piercing of ear 25, according to one embodiment of the disclosure. Lip 15 of female-tag container 14a is shown positioned below sample container 22 and clamp 18. Also shown in FIG. 7A is detachment of flap 16 from the stalk 9 of male ear-tag 7 by unhooking of holders 16c and movement of distal part of arm 16a.

Figure 7B:
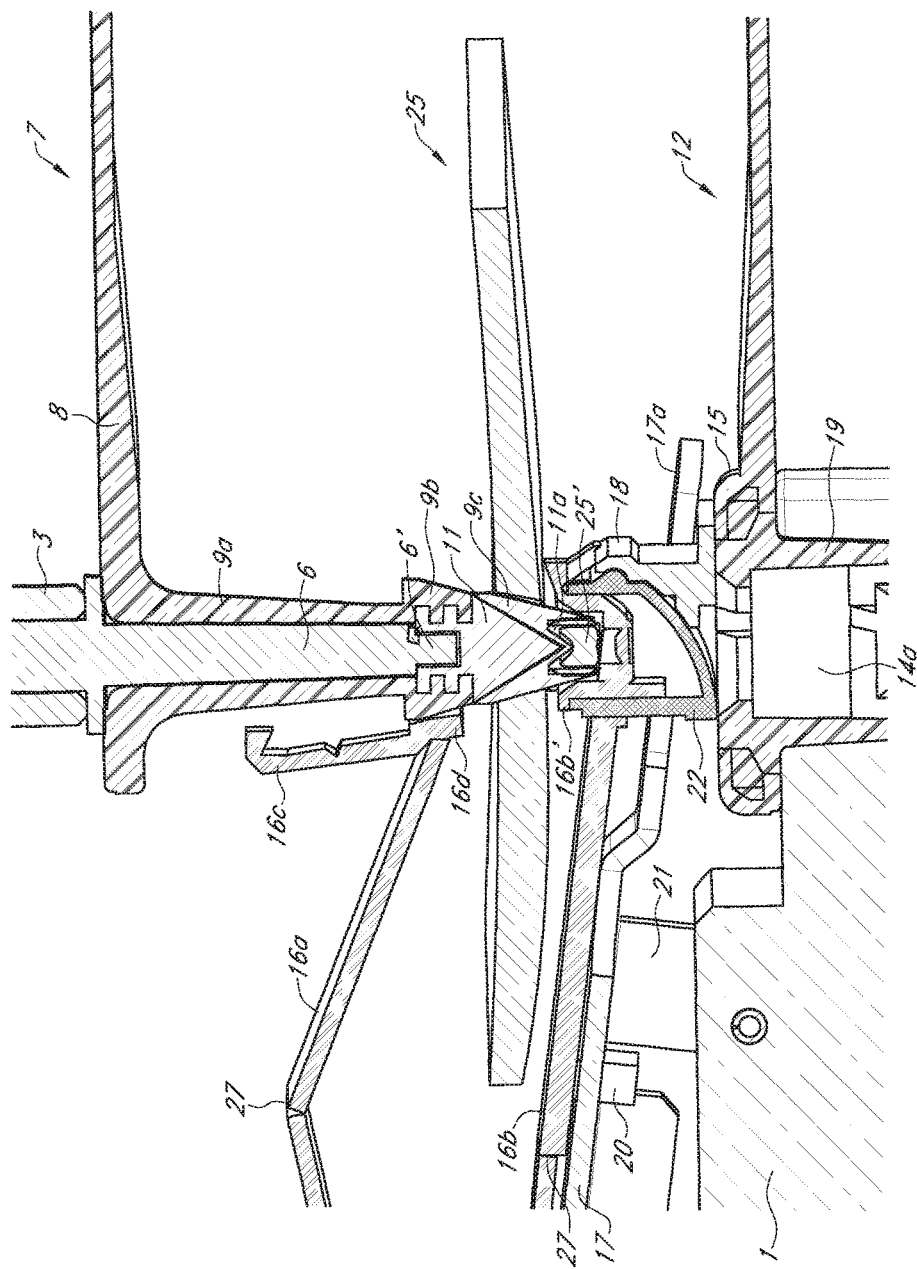
FIG. 7B depicts a cross-sectional view of FIG. 7A.

FIG. 7B depicts a cross-sectional view of FIG. 7A and shows stalk 9a of male tag 7 connected to pin holder 6 of pliers 1 on the inside. Stalk 9a continues into an inverted triangular portion 9b which internally comprises conical part 11 the top of which is designed to complementarily fit into pin tip 6'. Shank 9 is operable to be reversibly attached by means holder 16c to flap 16. Sample container 22 is shown having part of cutting element 9c including cutter 11a and ear-tissue sample 25' contained therein. Sample container 22 has an asymmetric shape on the bottom half. This asymmetric shape allows container 22 to tip transversely following cutting of tissue and the entry of conical part 11 of male ear-tag into the female ear-tag portion.

In FIG. 7B, since ear tissue 25 is already cut, holders 16c are shown detached and moving away from shank 9. Also depicted is cutting element 9c of male ear-tag 7, immediately below which is located cut ear-tissue sample 25' now inside container 22.

Figure 8A:
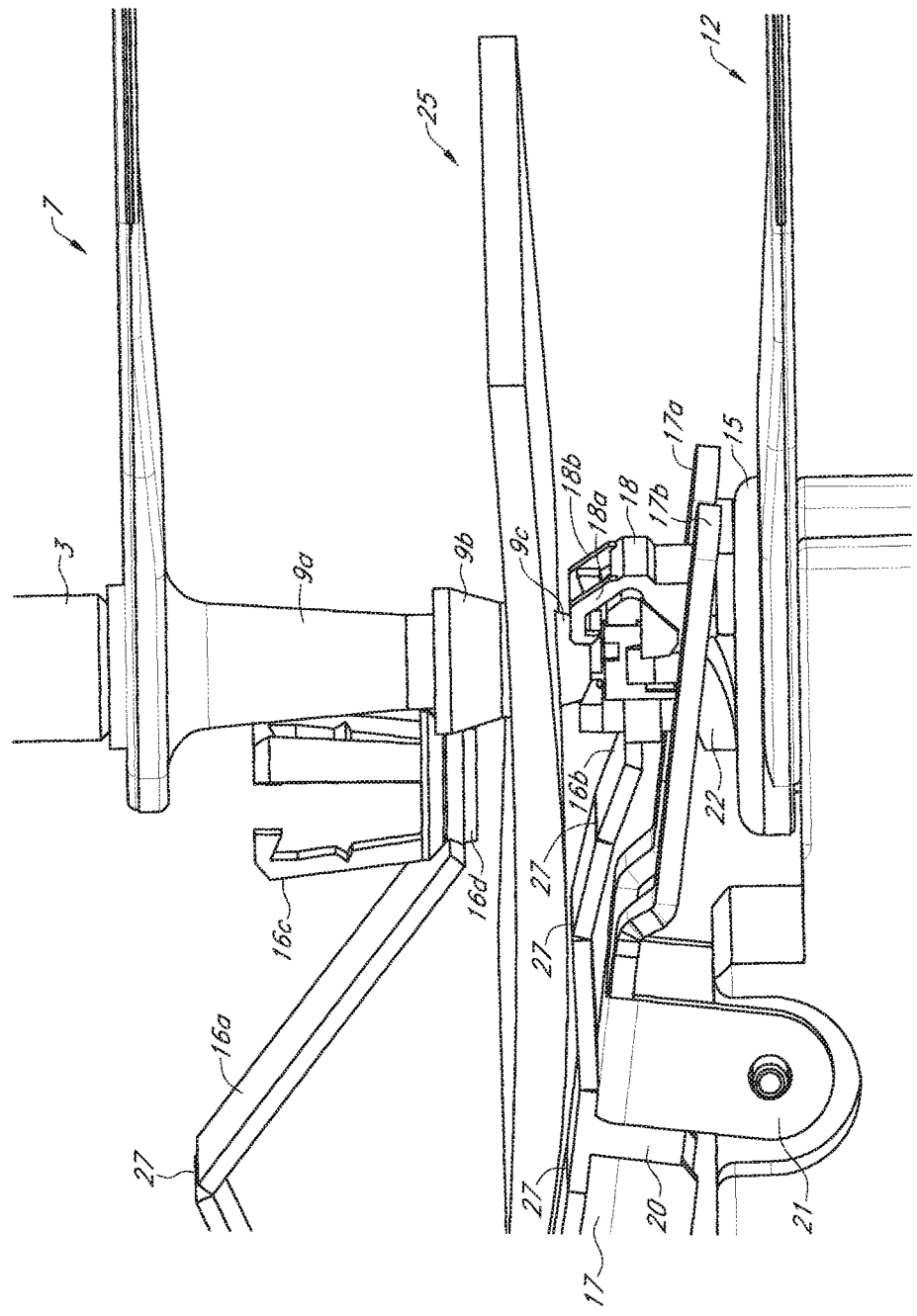
FIG. 8A depicts sample container with tissue sample and flap detaching from the ear-tag following ear piercing using the device of FIG. 3, according to one embodiment of the disclosure.
Figure 8B:
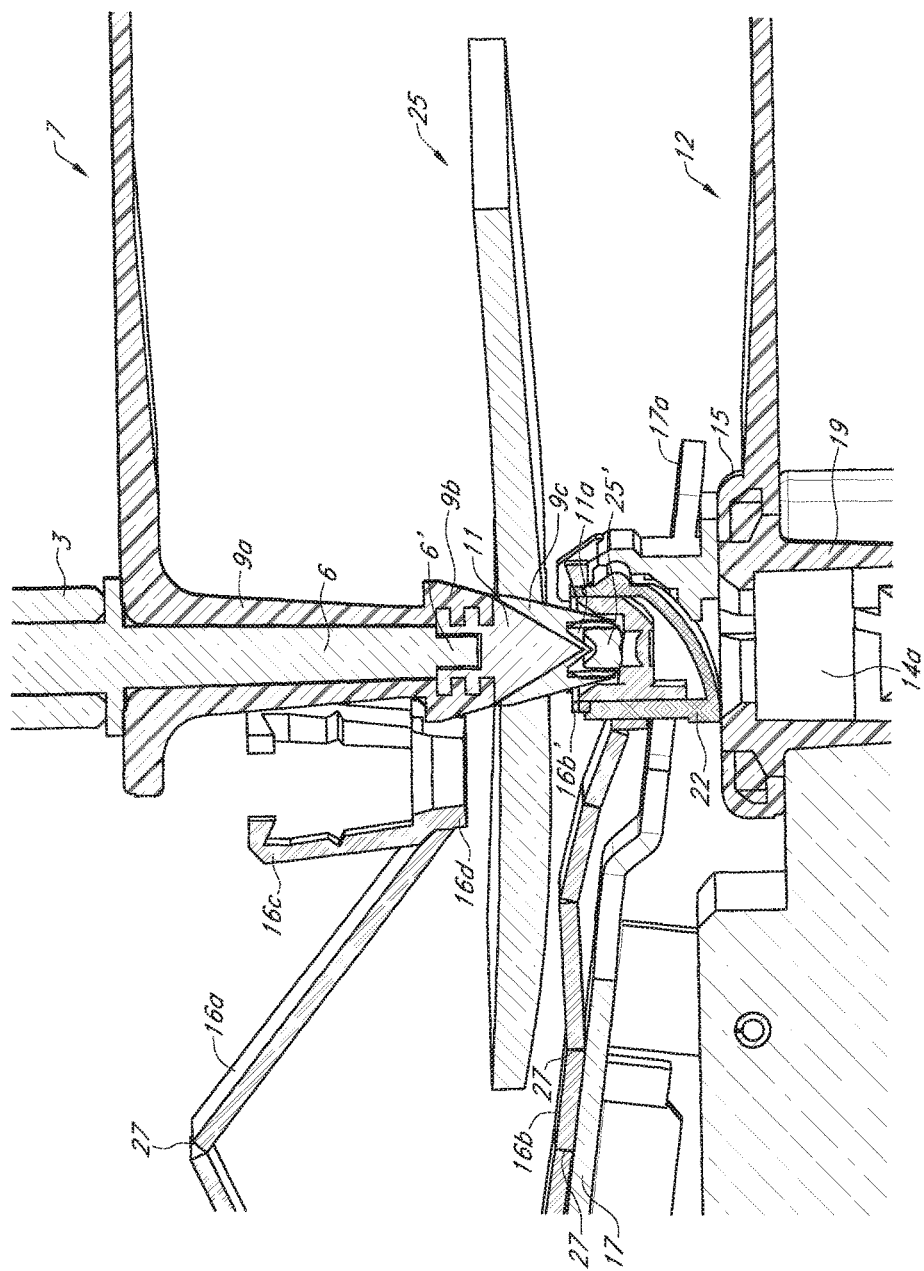
FIG. 8B depicts a cross-sectional view of FIG. 8A.

FIG. 8A depicts another close-up view of sample container 22 with tissue sample (not shown) and holders 16c detached from male ear-tag 7 following ear piercing using device 10 of the disclosure, according to one embodiment. Element 16b' has been pushed down by male tag and the outer parts of 16b' push clamp 18 to the side until clamp 18 no longer supports or holds the position of sample container 22 in the path of movement of male tag 7. FIG. 8B depicts a cross-sectional view of FIG. 8A.

Figure 9A:
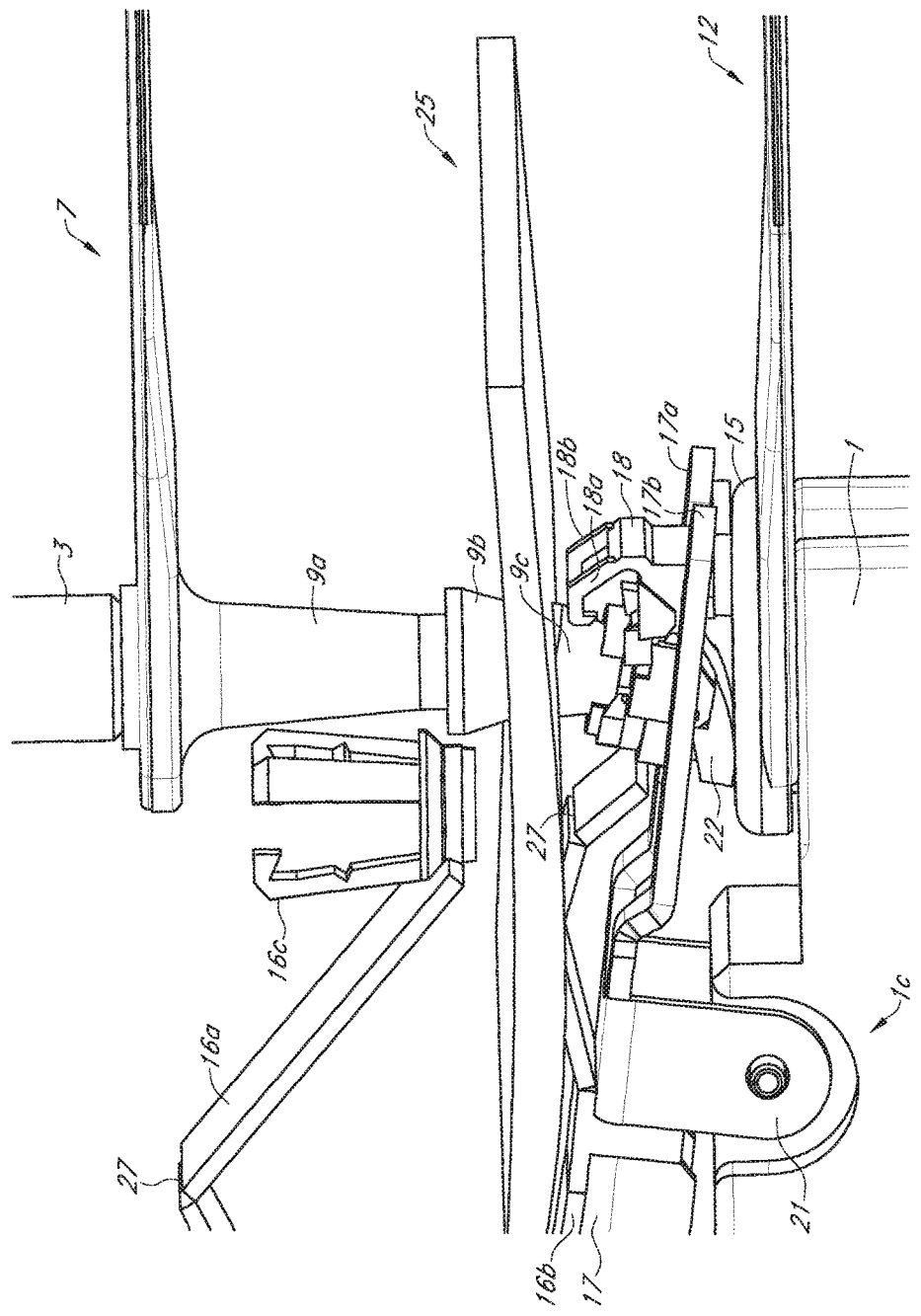
FIG. 9A depicts transverse movement of sample container with tissue sample by detachment of clamp elements and flap detaching from the ear-tag following ear piercing using the device of FIG. 3, according to one embodiment of the disclosure.
Figure 9B:
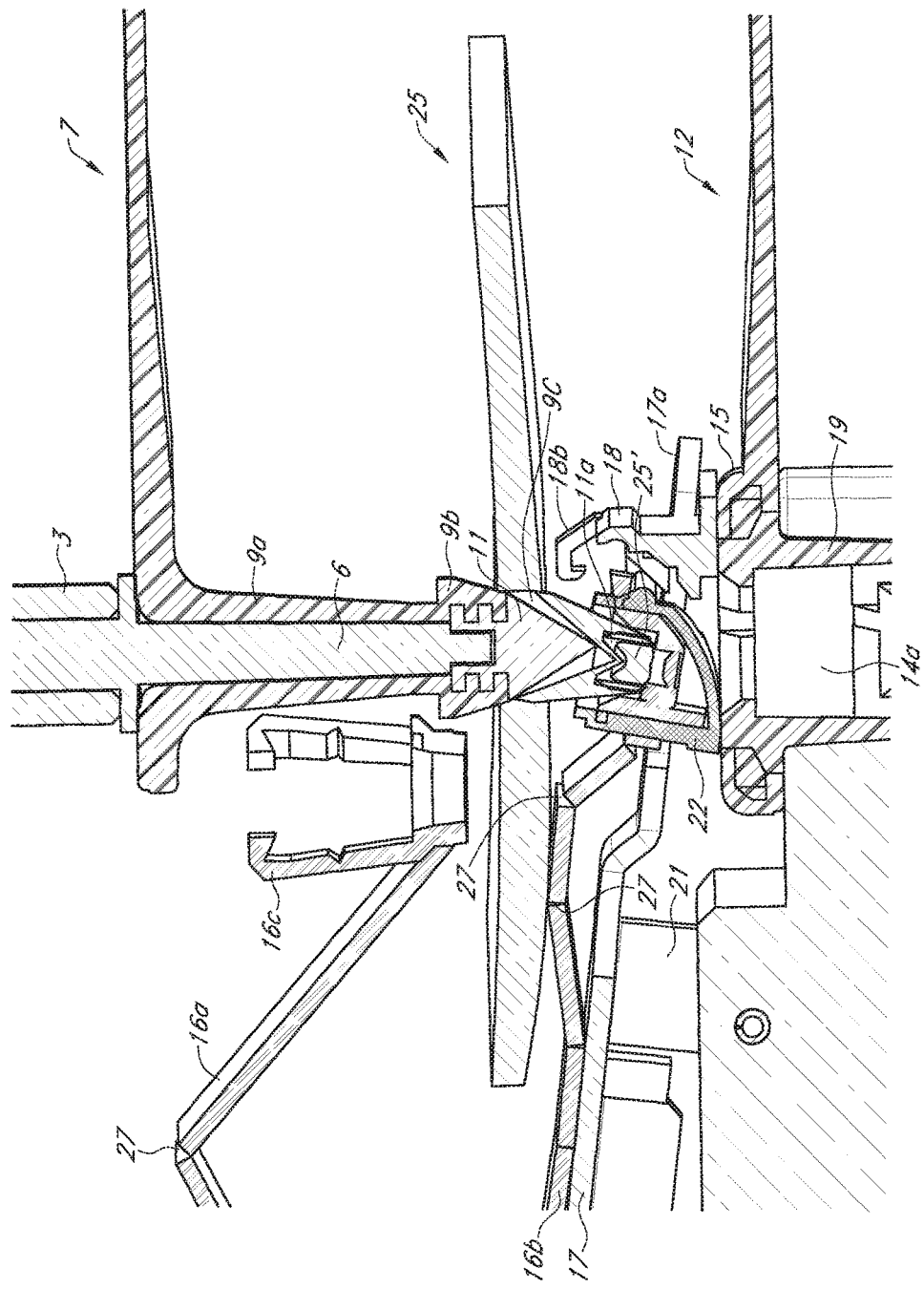
FIG. 9B depicts a cross-sectional view of FIG. 8A.

FIG. 9A depicts transverse movement of sample container 22 (which contains tissue sample 25') caused by entry of conical part 11 of male tag 7 past sample container 22 and through hole 14 into container 14a. Clamps 18a and 18b detach from container 22 as the container 22 tips transversely allowing container 22 to move away and make space for male tag to enter female tag. Element 16b' has been pushed down by male tag and the outer parts of 16b' push clamp 18 to the side until clamp 18 no longer supports or holds the position of sample container 22 in the path of movement of male tag 7. FIG. 9B depicts a cross-sectional view of FIG. 9A.

Figure 10A:
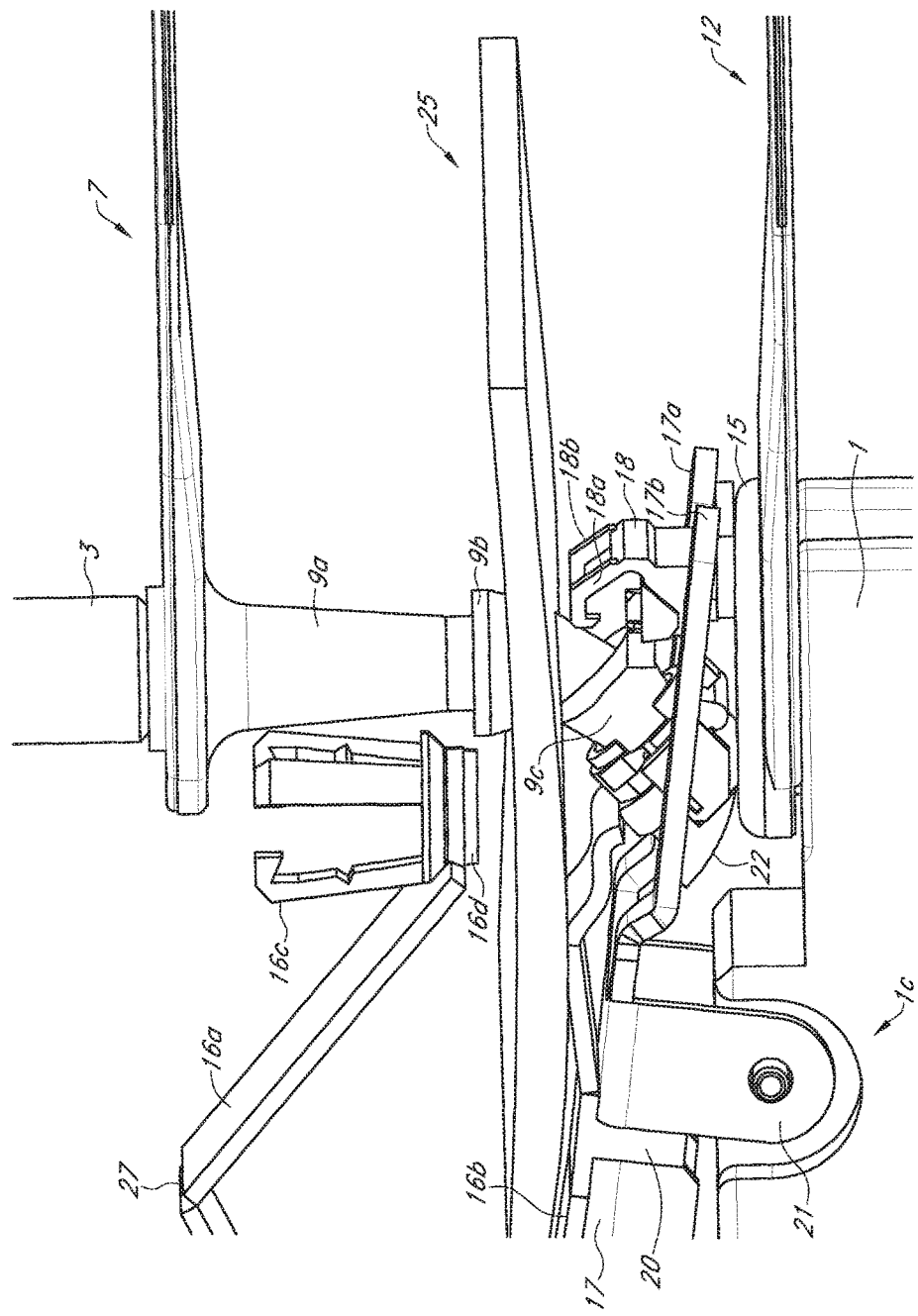
FIG. 10A depicts further transverse movement of sample container with tissue sample and shows detachment of pin tip of pliers to form lid on sample container using the device of FIG. 3, according to one embodiment of the disclosure.
Figure 10B:
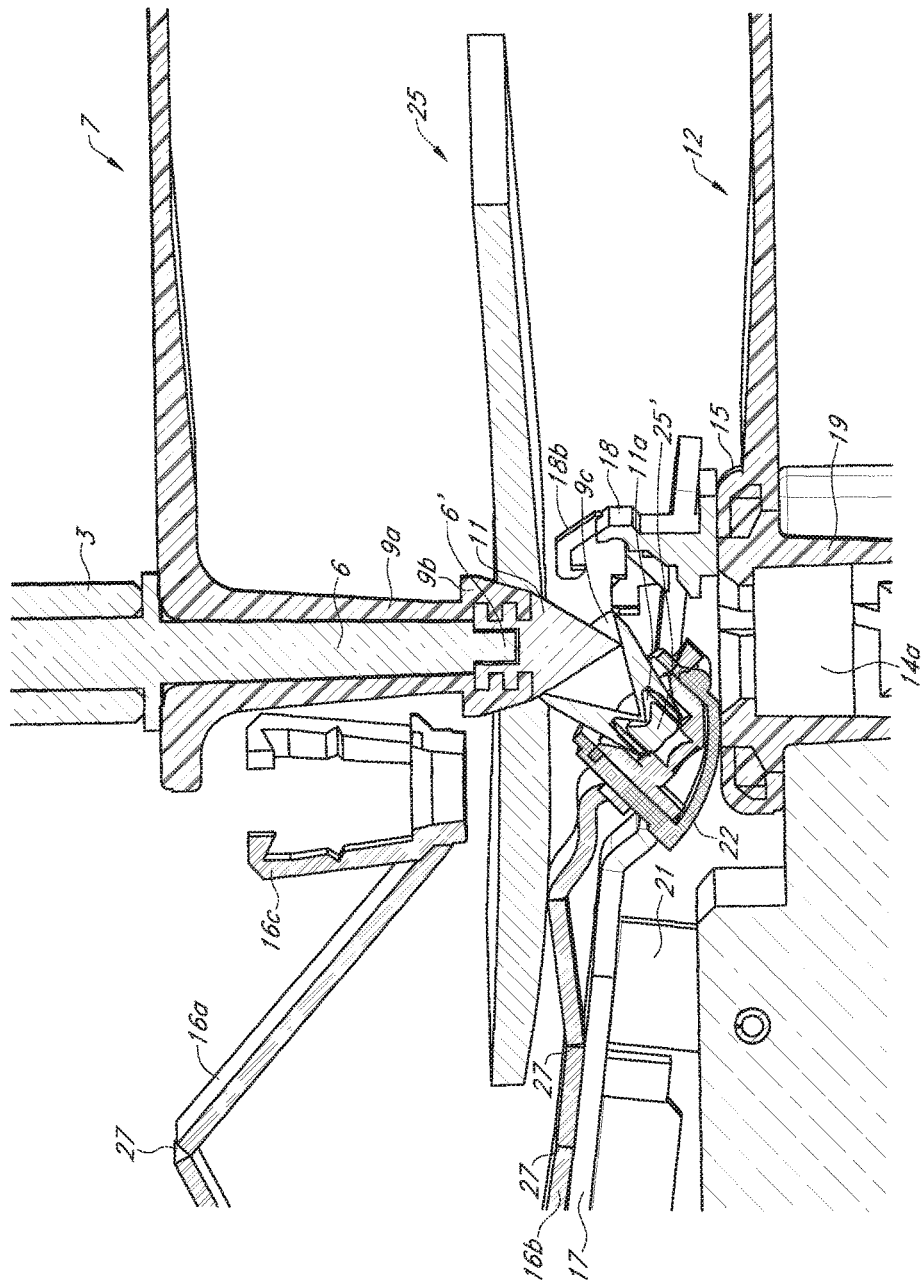
FIG. 10B depicts a cross-sectional view of FIG. 10A.

FIG. 10A depicts further transverse movement of sample container 22 with tissue sample (not shown) away from male tag 7 and shows detachment of part 9c of male tag 7 to form a lid on sample container 22 according to one embodiment of the disclosure. FIG. 10B depicts a cross-sectional view of FIG. 10A and shows parts 9c forming a lid on sample container 22 at its top side to seal in collected tissue sample 25'. In some embodiments, lid 9c forms an air-tight seal keeping tissue sample 25' protected. In some embodiments, sample container 22 will have a desiccant inside to keep tissue sample 25' in-tact. Desiccant can be previously placed in container 22.

Figure 11A:
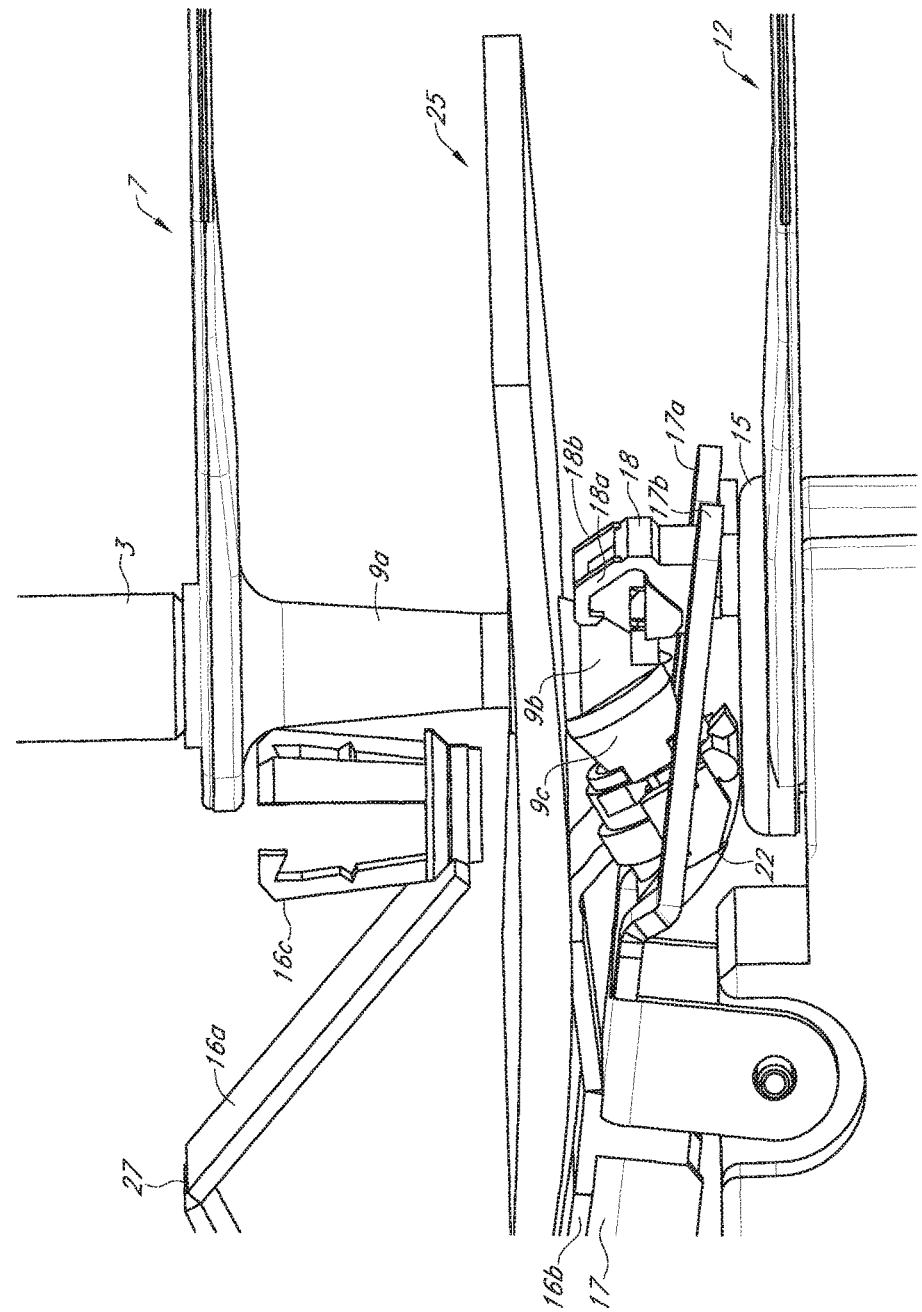
FIG. 11A depicts movement of male-tag tip toward female-tag following transverse movement of sample container when using the device of FIG. 3, according to one embodiment of the disclosure.
Figure 11B:
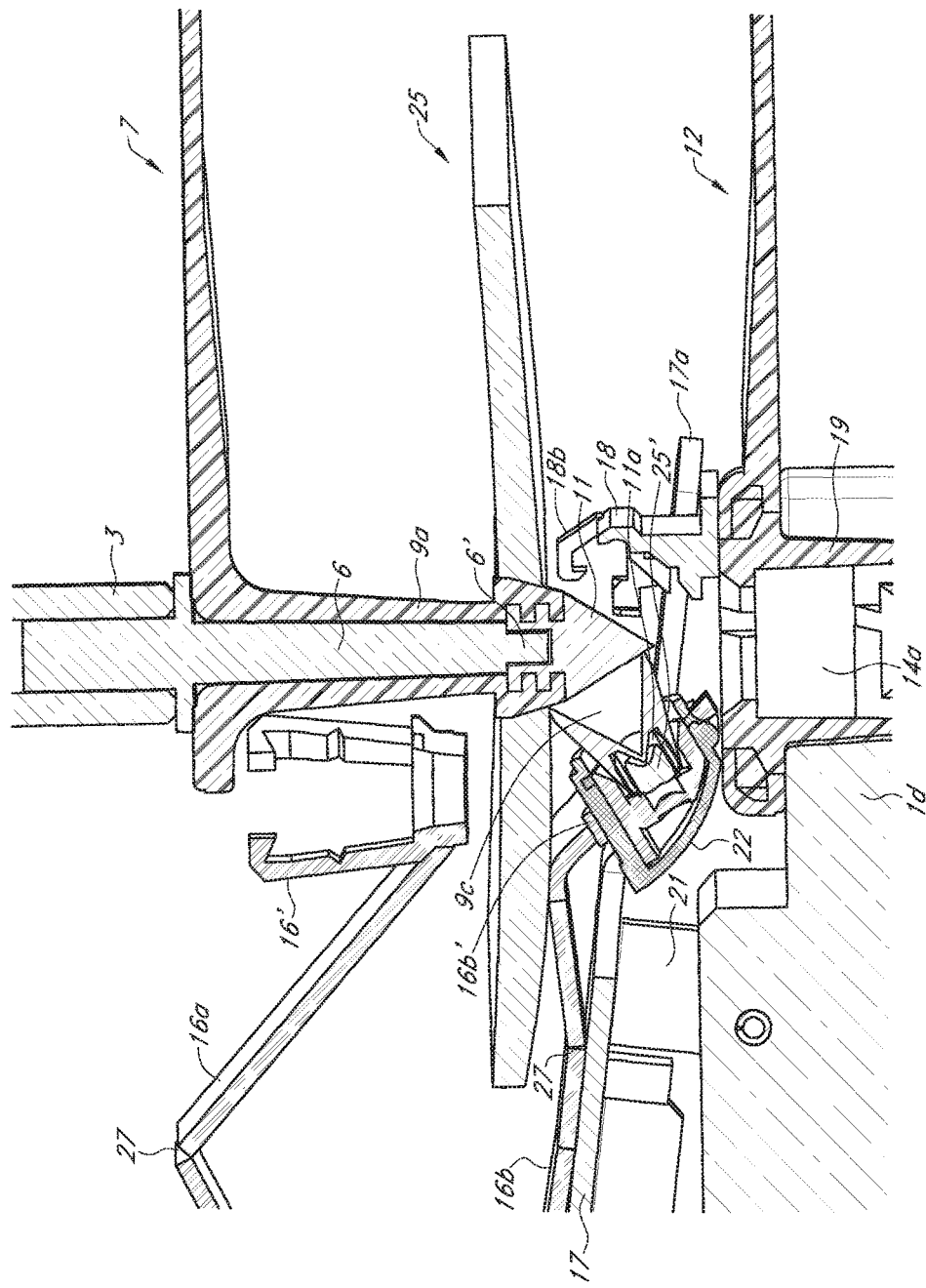
FIG. 11B depicts a cross-sectional view of FIG. 11A.

FIG. 11A depicts sample container 22 moved out completely and movement of male-tag tip 9b toward female-tag hole 14 and chamber 14a. FIG. 11B depicts a cross-sectional view of FIG. 11A and shows cut sample ear tissue 25' located in the sample container 22 now covered with 9c which now forms a lid 9c on container 22.

Figure 12A:
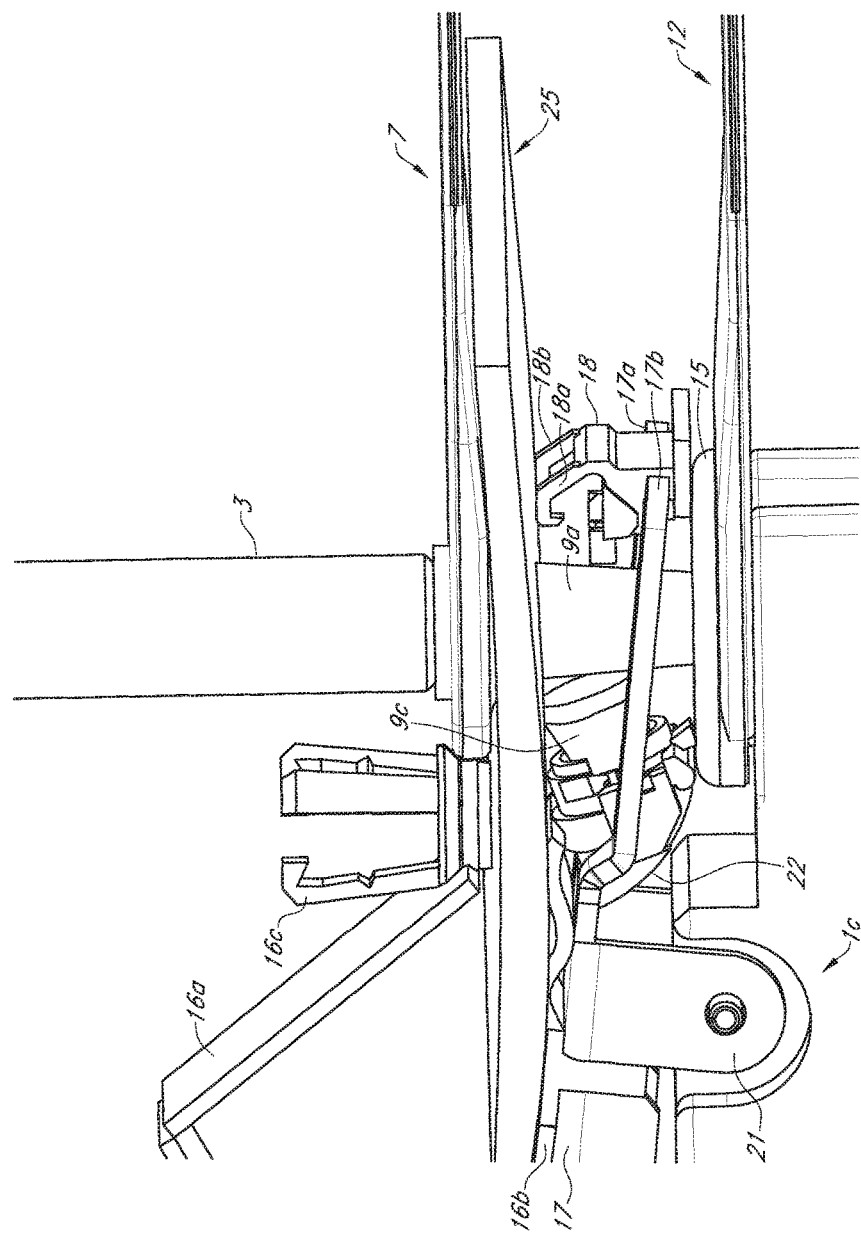
FIG. 12A shows male ear-tag and female ear-tag parts sealing to cause attachment of ear-tag to ear after using the device of FIG. 3, according to one embodiment of the disclosure.
Figure 12B:
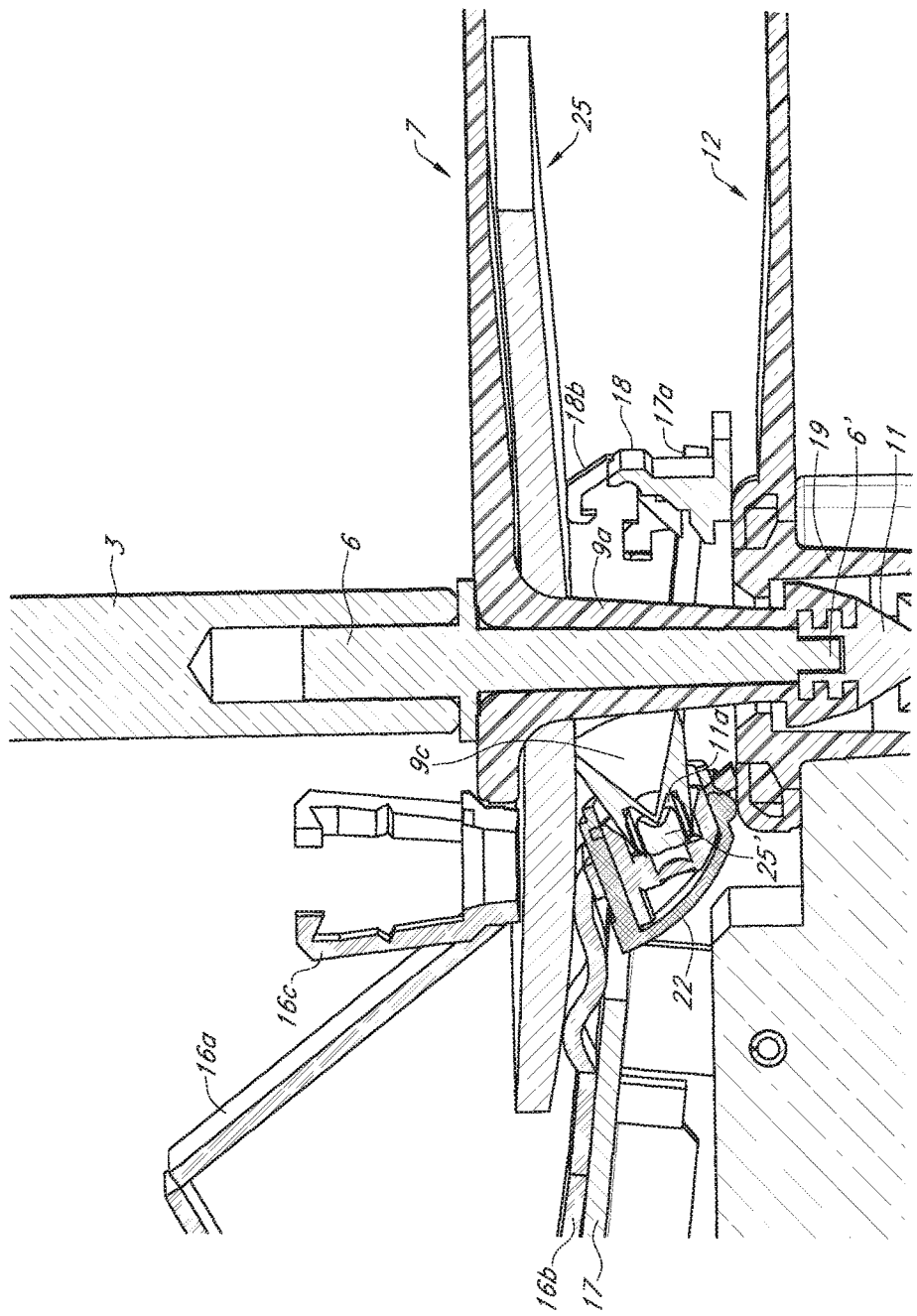
FIG. 12B depicts a cross-sectional view of FIG. 12A.

FIG. 12A shows male ear-tag shank 9 inserted into female ear-tag chamber 14a thereby completing attachment of ear-tag to ear 25 using device 10 according to one embodiment of the disclosure. FIG. 12B depicts a cross-sectional view of FIG. 12A and shows location of element 11 and part 9b of male ear-tag into chamber 14a of female part of ear-tag 12. Container 22 with sample 25' and lid 9c are also depicted.

Figure 13:
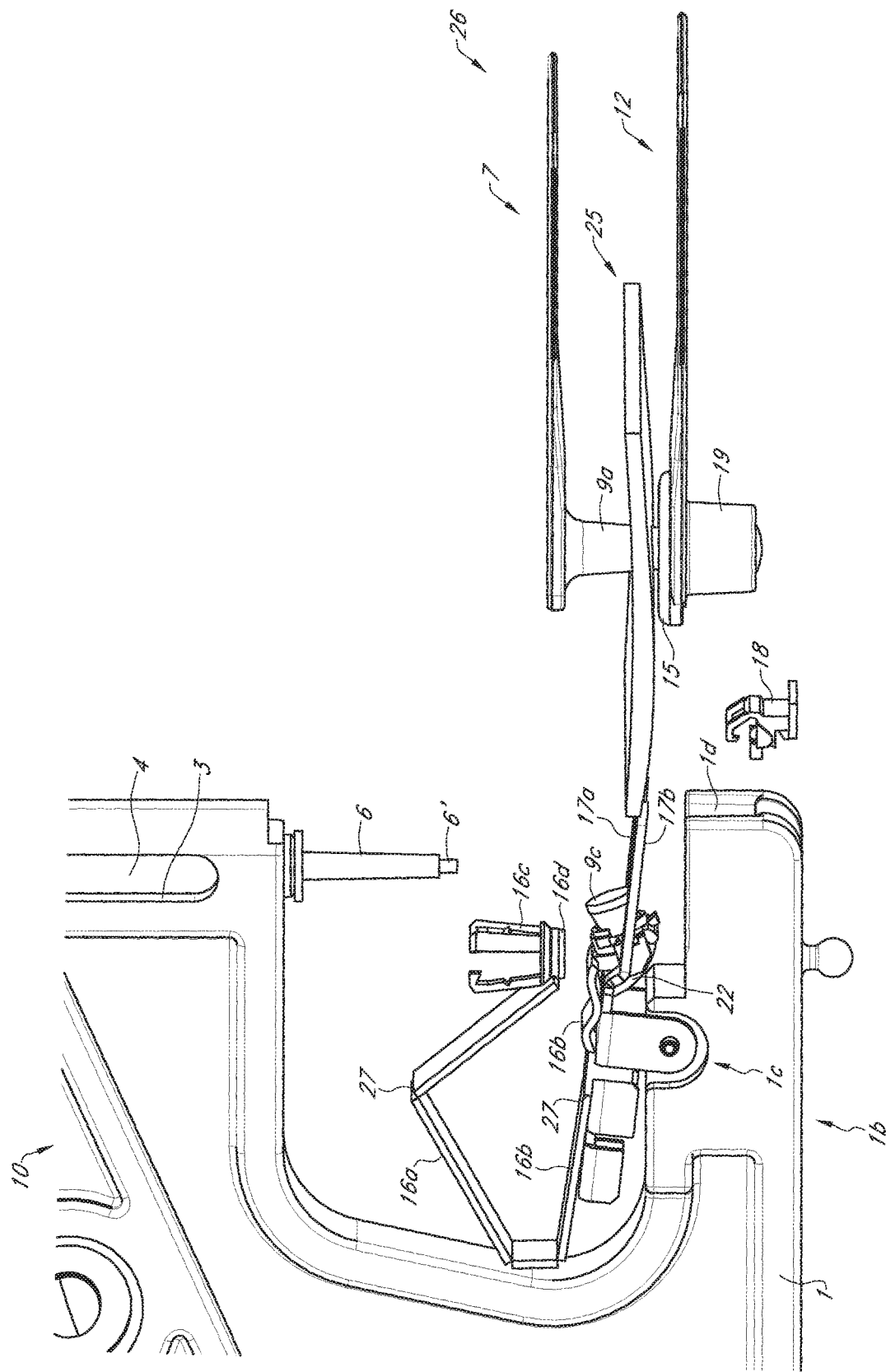
FIG. 13 shows ear-tag attached to ear and ear moved away from the device of FIG. 3, according to one embodiment of the disclosure.

FIG. 13 shows ear-tag 26 attached to ear 25 and ear with tag moved away from device 10. Clamp element 18 is also detached from device 10.

Figure 14A:
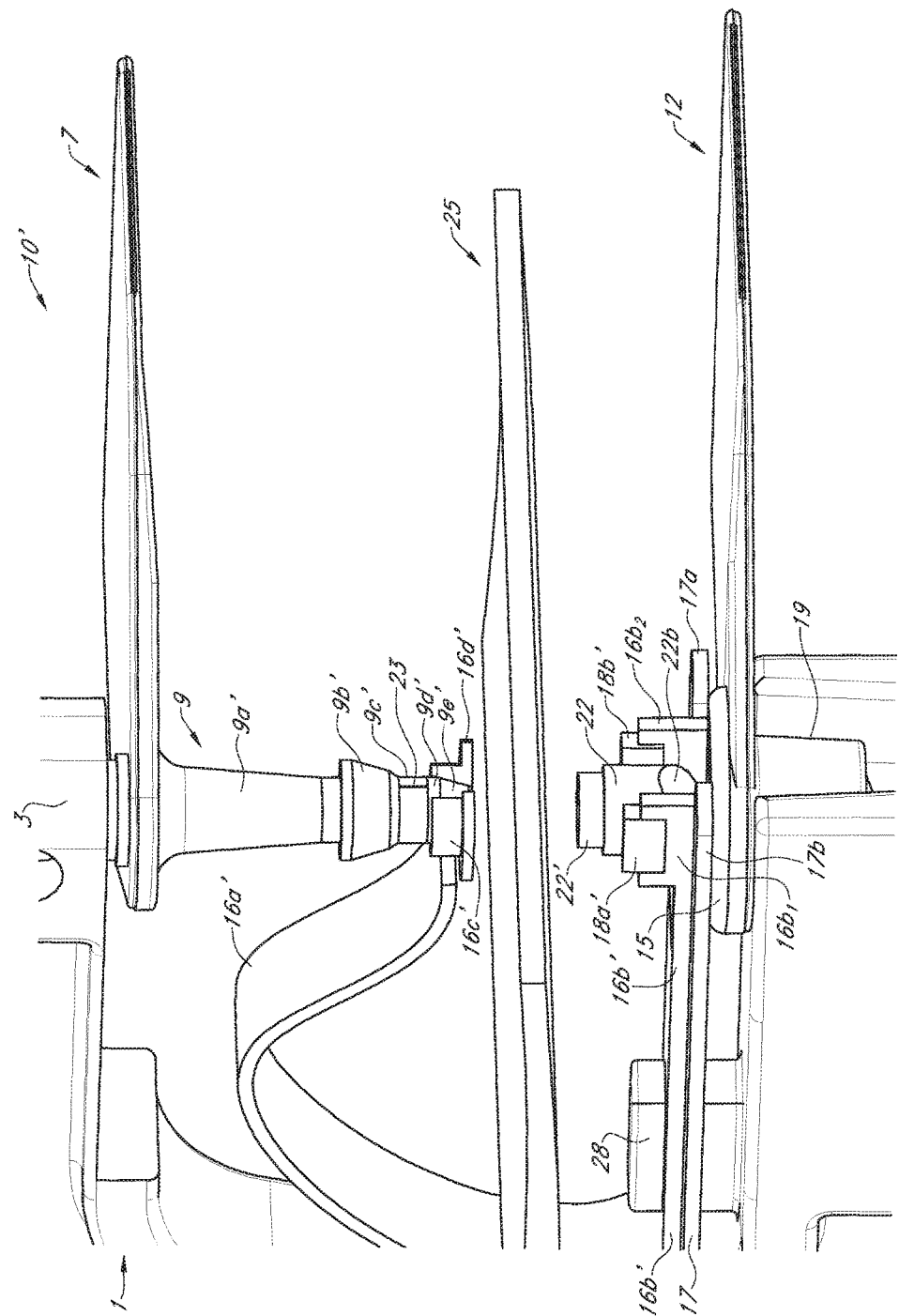
FIG. 14A depicts a side view of another embodiment of a device of the disclosure and depicts a close-up side view showing association of both male and female ear-tag parts with pliers, flap, downholder clip and clamps and positioning of an ear, to which the ear-tag is to be attached and from which sample tissue is to be removed according to one embodiment of the disclosure.

FIG. 14A depicts a schematic side view of another exemplary apparatus 10' for applying an identity-tag and removing a sample tissue, according to another embodiment of the disclosure. Apparatus 10' is also tamper-resistant as described in above sections for apparatus 10. Apparatus 10' comprises pliers 1, ear-tag components comprising male-part of an ear-tag 7 and female part of the ear-tag 12. In some embodiments, pliers 1 and ear-tag components have features as described in sections above for apparatus 10. Apparatus 10' can have variations in one or more parts including flap components 16' (comprising 16a', 16b' . . . and the like), downholder clip 17' (17a', 17b' . . . and the like), clamping elements 18', and/or sample container and its associated components.

FIG. 14A depicts a side-view of device 10' of the disclosure shows the association of both male ear-tag 7 and female ear-tag 12 parts with pliers 1, flap 16', downholder clip 17' and clamp element 18' and further shows the positioning of an ear 25, to which the ear-tag is to be attached to and from which sample tissue is to be removed according to one example embodiment.

As shown in this embodiment, flap 16' has two arms 16a' and 16b'. Arm 16a' has a curved arc shape with its proximal end continuing to the beginning of arm 16b'. Distal end of arm 16a' joins holder 16c' and base 16d' which removably attach to distal end of shank 9 of male tag 7. Arm 16b' branches into two forks: 16b1' and 16b2' at its distal end and a space or cavity is disposed in between the two forks wherein sample container 22 can fit. Flap 16' is attached to pliers 1 by means of a connector 28. Connector 28 can be any connector such as but not limited to a screw which fits into a throughhole in 16, a clip that can hold in place parts 16' (and 17' in some embodiments) onto pliers 1, a projection of pliers 1 having a hole shaped to fit flap 16' into it (as well as downholder clip 17' in some embodiments), a magnetic connector having a bottom and top magnet (both shown as 28) between which flap 16' (as well as downholder clip 17' in some embodiments) can be held by magnetic forces. In some embodiments, flap 16' can be made of rigid or flexible plastics or metal sheets. Typical pliers 10 or 10' are made of metal and/or rigid plastics.

Downholder clamp 17' also branches into two arms 17a' and 17b' which lie adjacent to the edges of arm 16b' and forks 16b1' and 16b2'.

Sample container 22 has an asymmetrically shaped bottom side 22b similar to that described in embodiments above. Sample container 22 has a top-part 22' disposing a cavity or hole therein to allow male-tag part to enter in. Top part 22' includes a closed counter plate that helps punching the tissue sample. Part 22' also acts as intermediate part between male tag 7 and clamps 18a and 18b. In use, when male tag 7 pushes part 22' down, part 22' pushes clamps 18a' and 18b' to the side.

In one embodiment, device 10' as depicted in FIG. 14A has clamp element 18' having clamps 18a' and 18b' is disposed on groves on forks 16b1' and 16b2'. Clamps 18a' and 18b' clamp sample container 22 in place during ear-piercing and ear-tissue extraction.

Figure 15A:
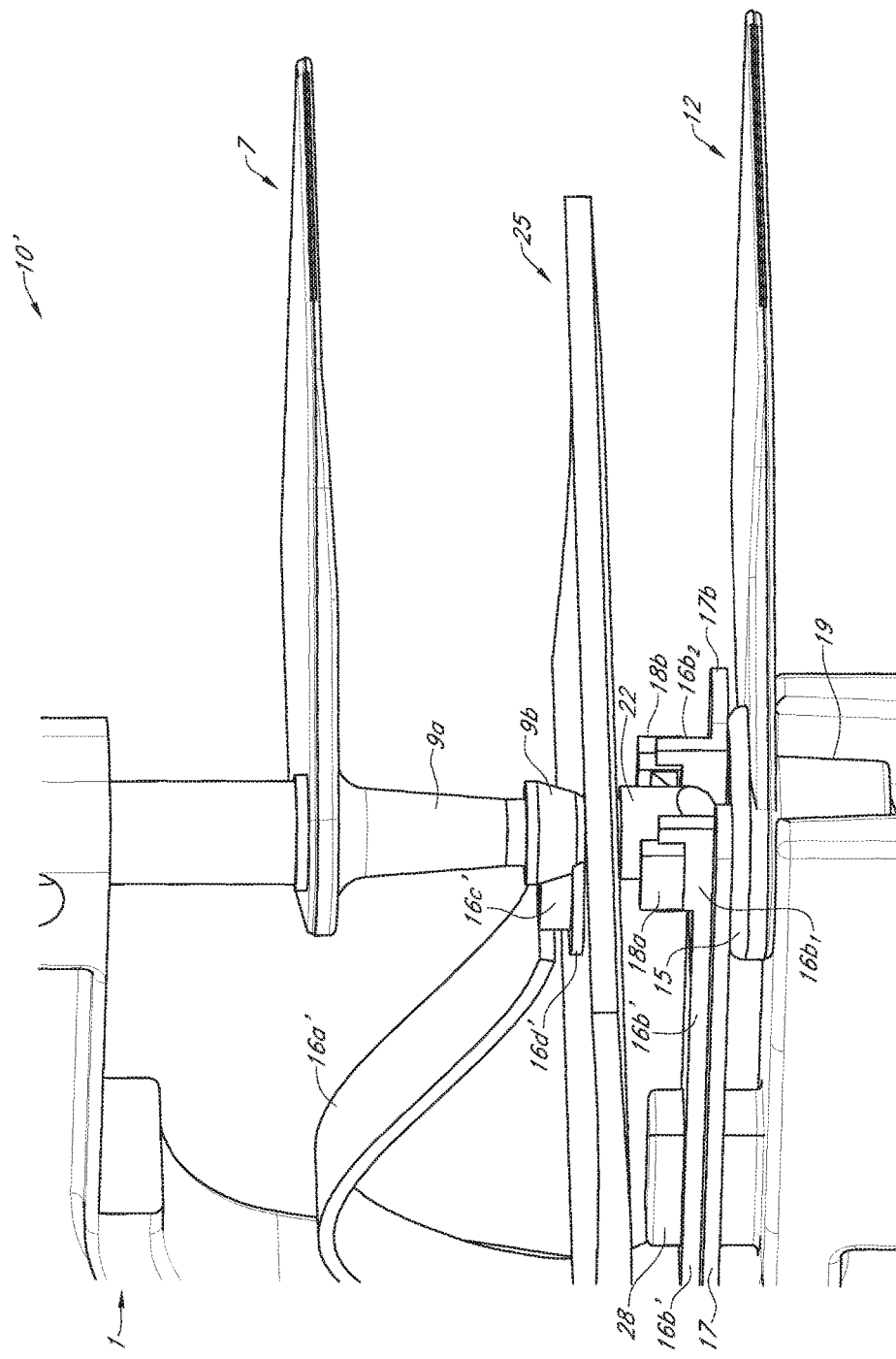
FIG. 15A depicts the device of FIG. 14A piercing through the ear, according to one embodiment of the disclosure.
Figure 15B:
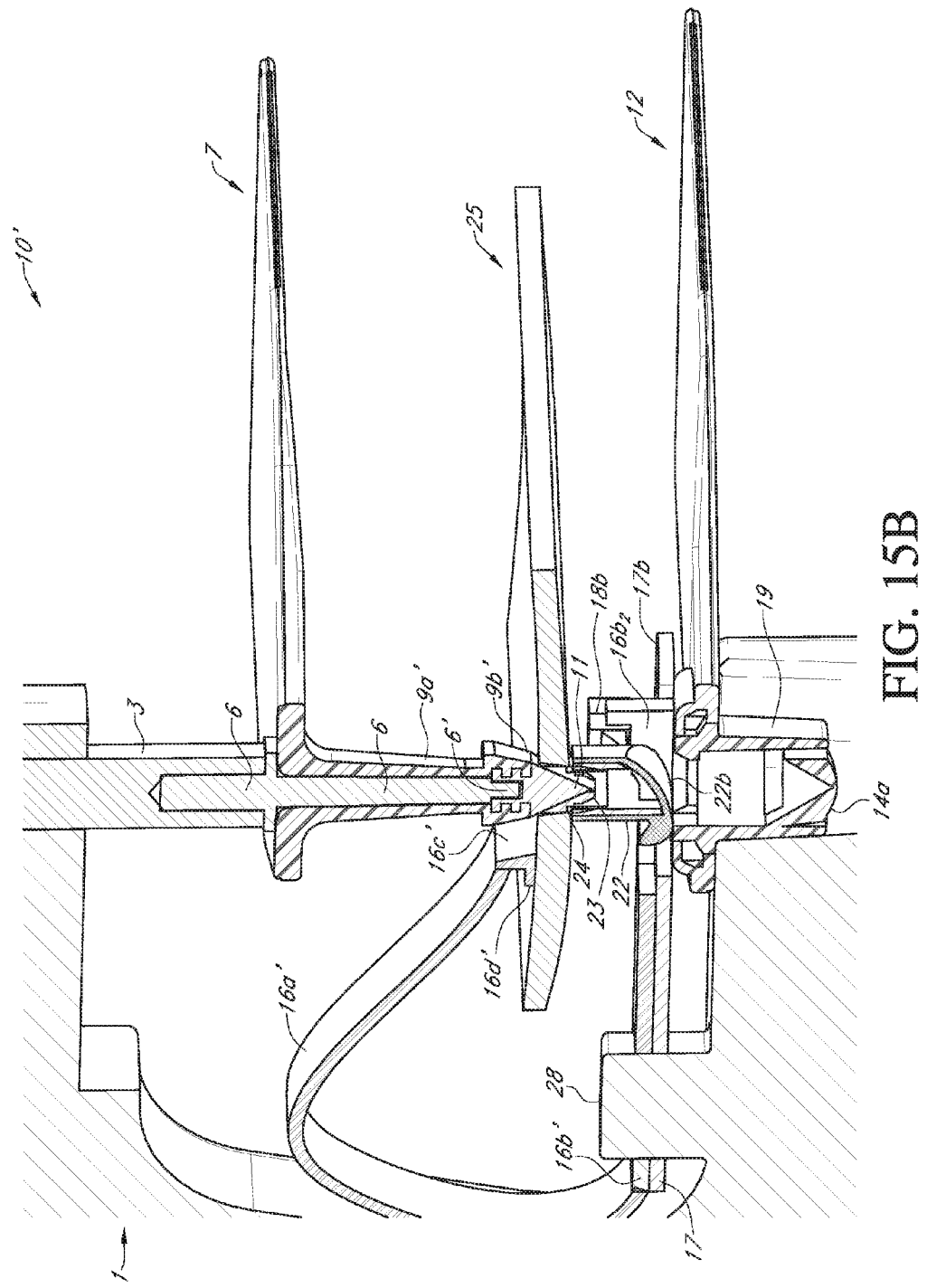
FIG. 15B depicts a cross-sectional view of FIG. 15A.
Figure 16A:
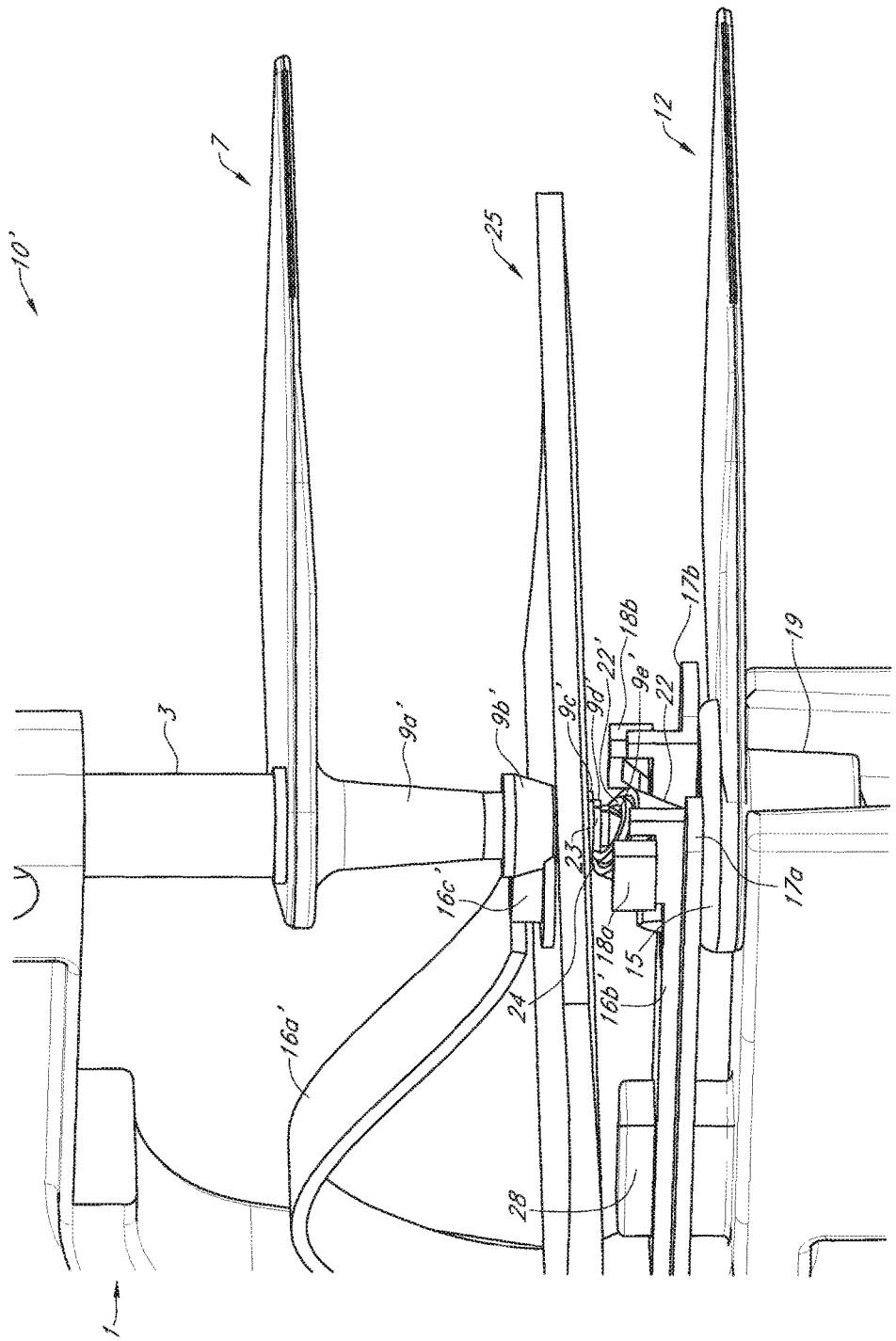
FIG. 16A depicts sample container with tissue sample detaching from the ear-tag following ear piercing during use of the device of FIG. 14A, according to one embodiment of the disclosure.
Figure 16B:
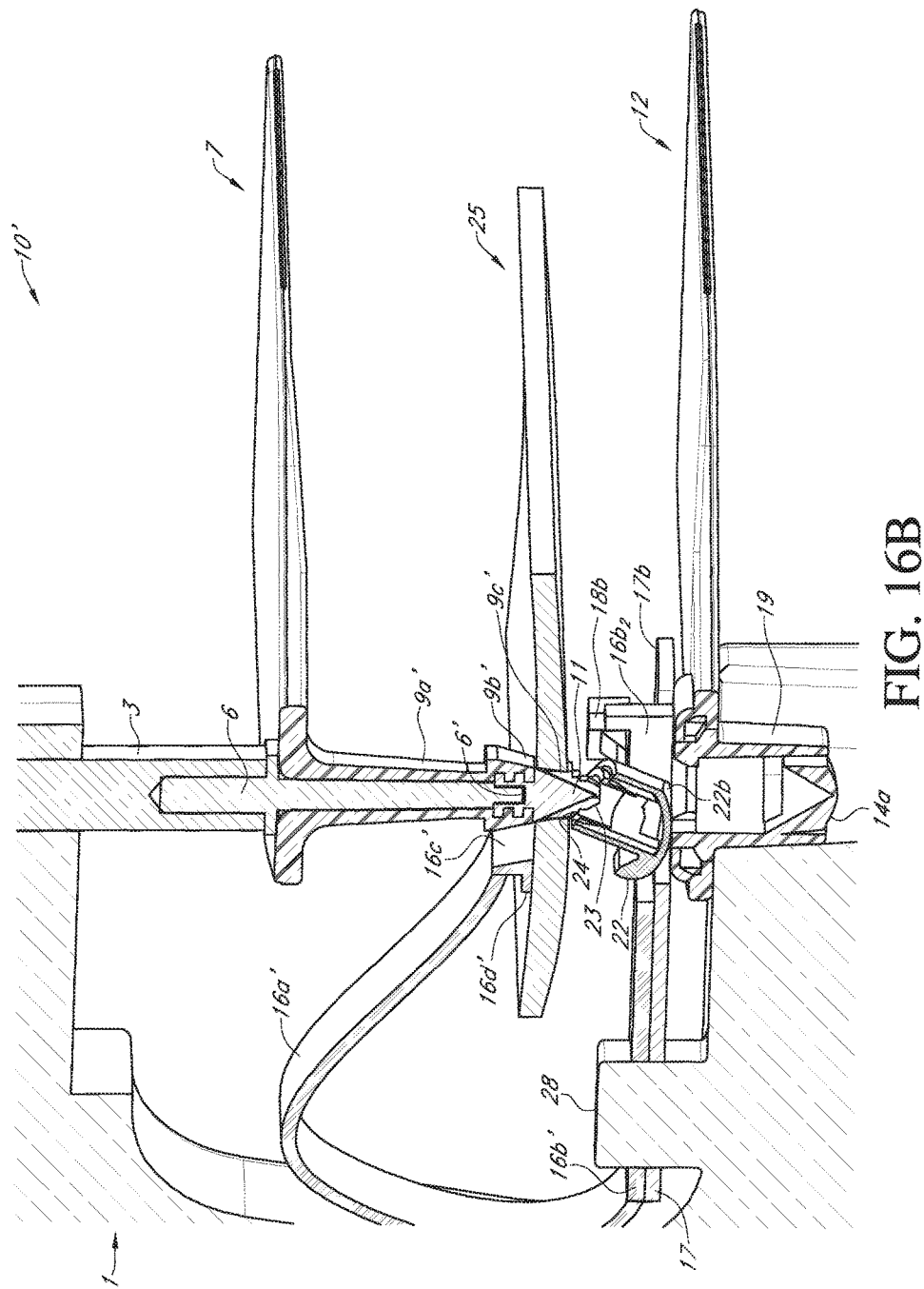
FIG. 16B depicts a cross-sectional view of FIG. 16A.
Figure 17B:
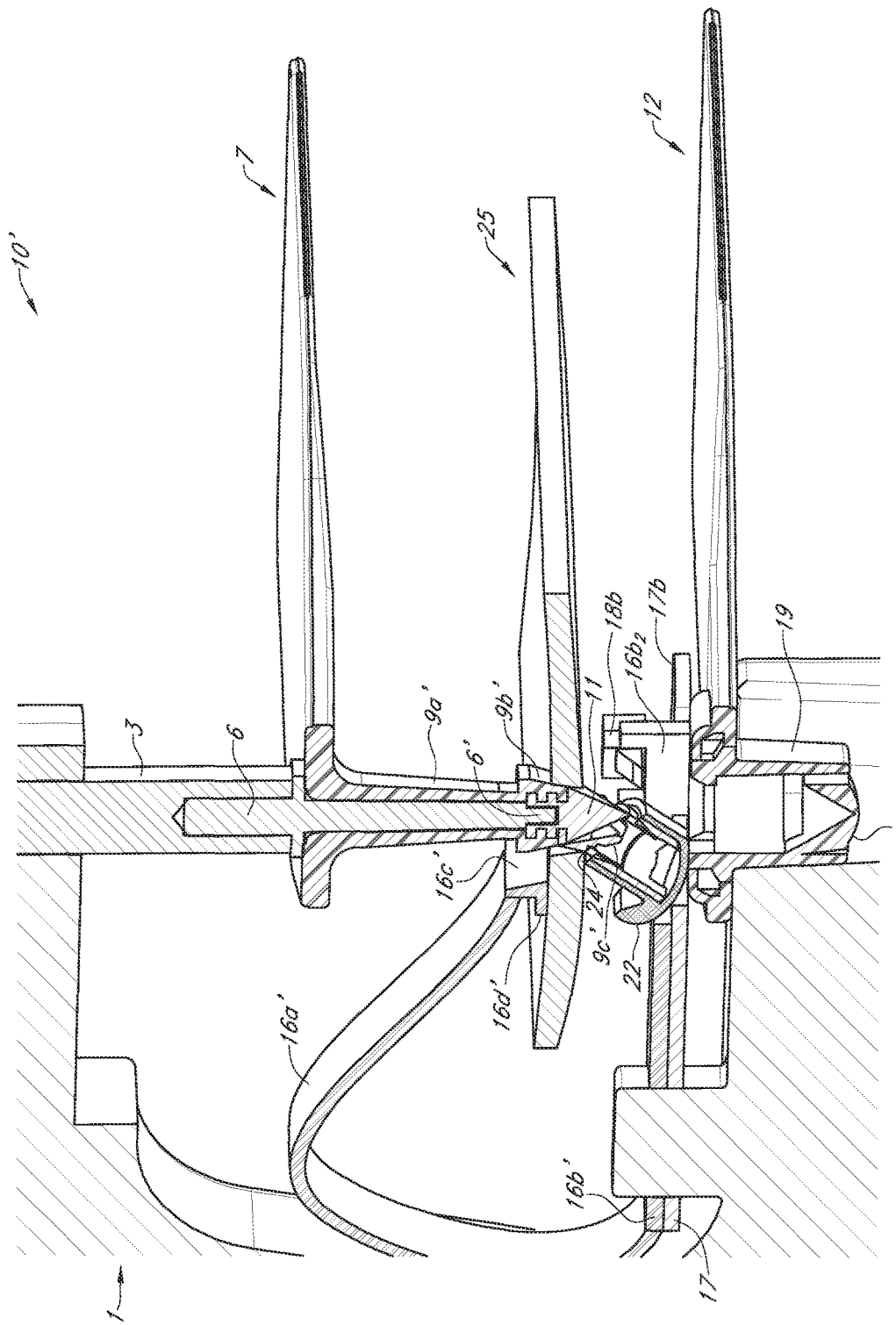
FIG. 17B depicts a cross-sectional view of FIG. 17A.

According to one embodiment, tissue cutter element (also referred to herein as punch) comprises upper part of punch 9c', lower part of punch 9d' and 9e', hinges 24 and slit 23 (not expressly shown in FIG. 14A, see FIGS. 15B, 16B and 17B). Tissue cutter element described in this embodiment of device 10' is different from tissue cutter element 9c described above for device 10.

Figure 14B:
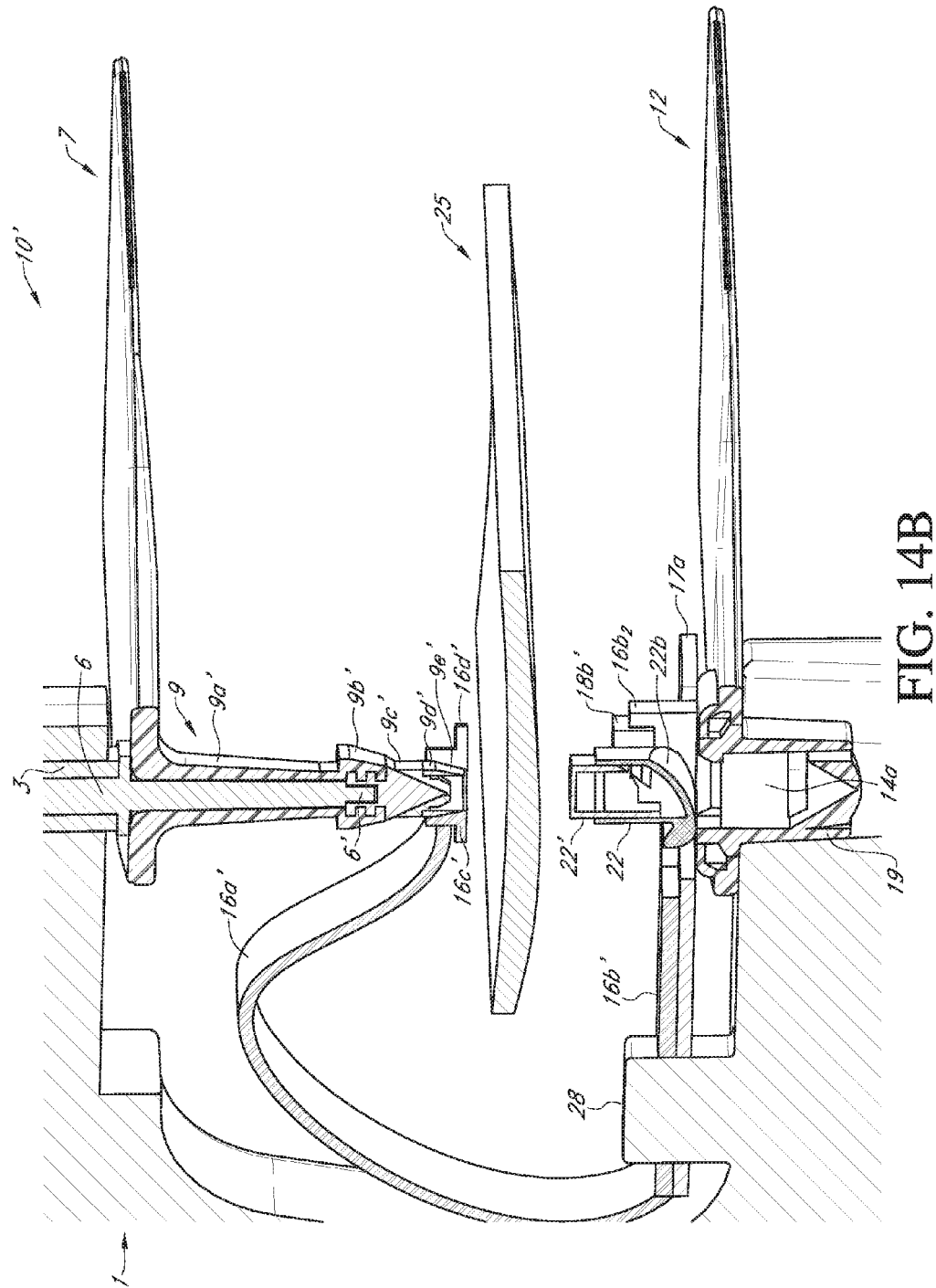
FIG. 14B depicts a cross-sectional view of FIG. 14A.

FIG. 14B depicts a cross-section of device 10' as shown in FIG. 14A. Inside shank 9 of male tag 7, conical element 11 is disposed the top part of which fits into pin tip 6' of pliers 1 similar to that described for device 10 in sections above. FIG. 14B shows further details of 9c', 9d', 9e', slit 23 and hinge 24. Conical tip of element 11 (bottom part of element 11) fits into female-tag container 14a.

In use of device 10' at both the starting position and during punching or tissue removal, hinge 24 is in its closed position. In this position slit 23 of the punch/tissue cutter element in the upper part 9c' of the punch is securely closed by the lower part 9d' and 9e' of the punch. In this position the punch sits stiffly on top of male tag 7 and can be pushed through ear 25 by male tag 7. Until the punch enters container 22, the sample container 22 is securely held in place by the clamps 18a and 18b.

FIG. 15A depicts device 10' having pierced through ear 25. Tissue cutting element/punch (comprising portions of 9c', 9d and 9e) is inserted into ear 25 and container 22. Clamps 18a and 18b already have been pushed to the side by the part 22' which has been pushed down by the male tag.

FIG. 15B depicts a cross-sectional view of FIG. 15A and shows movement of element 11 and punch into ear 25 and container 22. FIG. 15B also depicts location of container 22 directly above female-tag hole 14 and chamber 14a. FIG. 15B also depicts that the punch has penetrated the lid of 22' and that the part 22' has been pushed down by the punch.

FIG. 16A depicts sample container 22 with tissue sample (not shown) detaching from male part of ear-tag 7 following ear piercing during use of device 10', according to one embodiment of the disclosure. Details such as slit 23 and hinge 24 can be seen. Sample container 22 tips in a transverse direction such as to move away from the path of element 11 of male-tag 7. The asymmetrical shape of the bottom part 22b of sample container 22 facilitates the transverse movement in response to the force of descending part 9c' of male tag 7 having conical tip 11.

FIG. 16B depicts a cross-sectional view of FIG. 16A. As soon as clamping elements 18a' and 18b' are released by the downwards moving punch 9c', container 22 tips away. Lower part of punch 9d' and 9e' tip away with container 22 (as there is a form-locking connection between these two parts). As a result of this, lower part 9d' and 9e' of punch no longer encases upper part of punch 9c' and slit 23 of upper part of punch 9c' opens when shank 9 of male part 7 continues travelling downwards toward female tag container 14.

FIG. 17A depicts transverse movement of sample container 22 now containing tissue sample 25' (not expressly shown) and lower portion of male part of ear-tag 7 traveling through slit 23 of upper part of cutting element 9c' following ear piercing during use of the device 10' as shown in FIG. 14A, according to one embodiment of the disclosure. In use, part 11 will continue to traverse down into female tag container 14a while sample container 22 with tissue sample 25' and parts of 9c' are released from male punch 7 to form a lid 9c' over container 22.

FIG. 17B depicts a cross-sectional view of FIG. 17A and shows parts 9d' and 9e' forming a lid on sample container 22 at end 22' to seal in the collected tissue sample 25' (not expressly shown). In some embodiments, the seal formed is an air-tight seal. In some embodiments, lid comprising 9d' and 9e' forms an air-tight seal keeping tissue sample 25' protected. In some embodiments, sample container 22 will have a desiccant inside to keep tissue sample 25' (not shown in figure) in-tact.

Figure 18A:
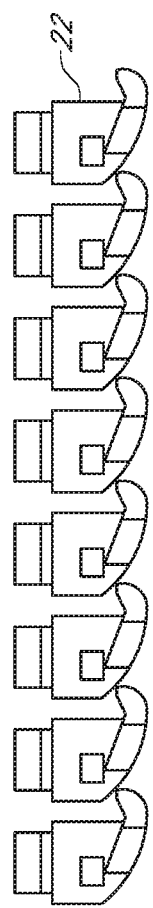
FIG. 18A depicts a two-dimensional view of sample containers of the disclosure arranged in an array with their asymmetrical bottom parts showing alignment as the subsequent container fits into the grove of the asymmetric portion of the previous container, according to one embodiment of the disclosure.
Figure 18B:
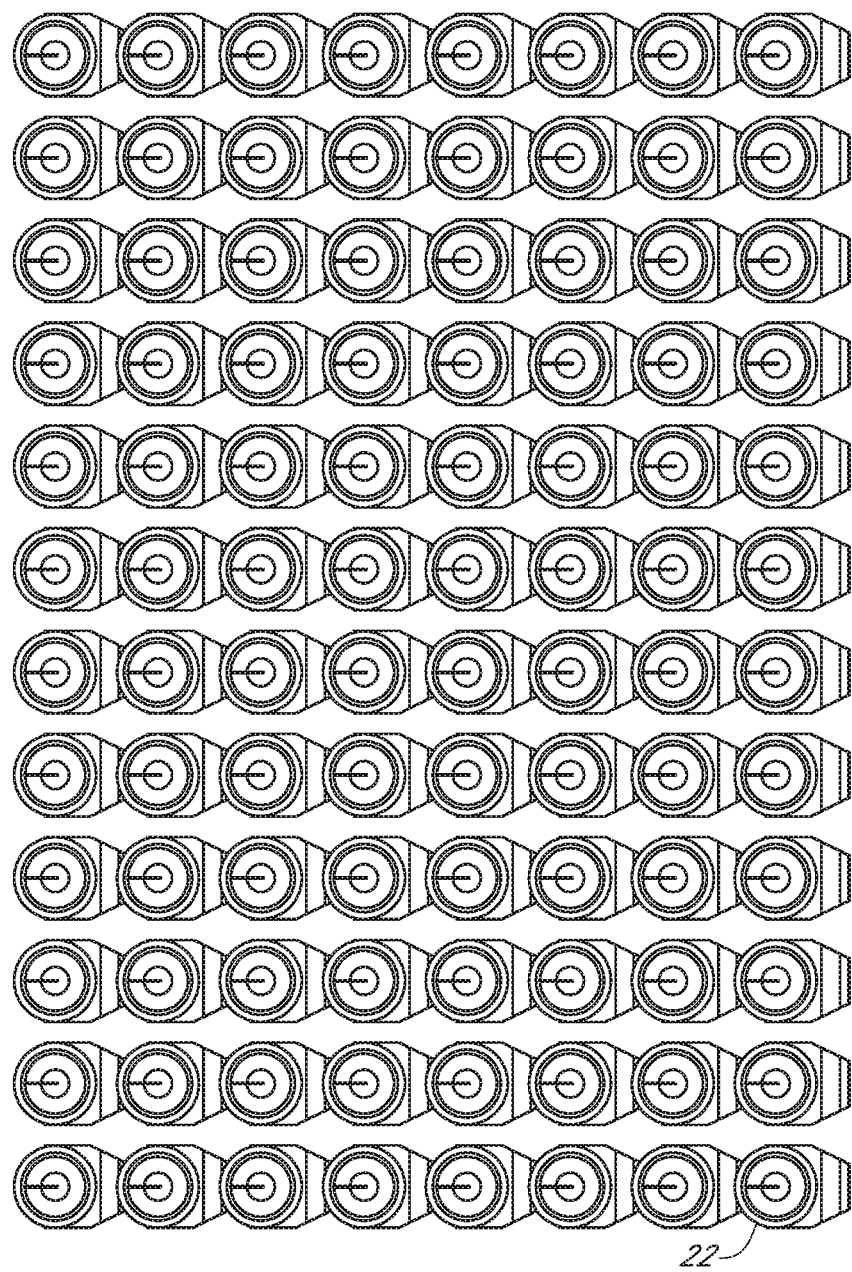
FIG. 18B depicts a top view of an array of sample containers of the disclosure arranged in a 96-well format, according to one embodiment of the disclosure.
Figure 18C:
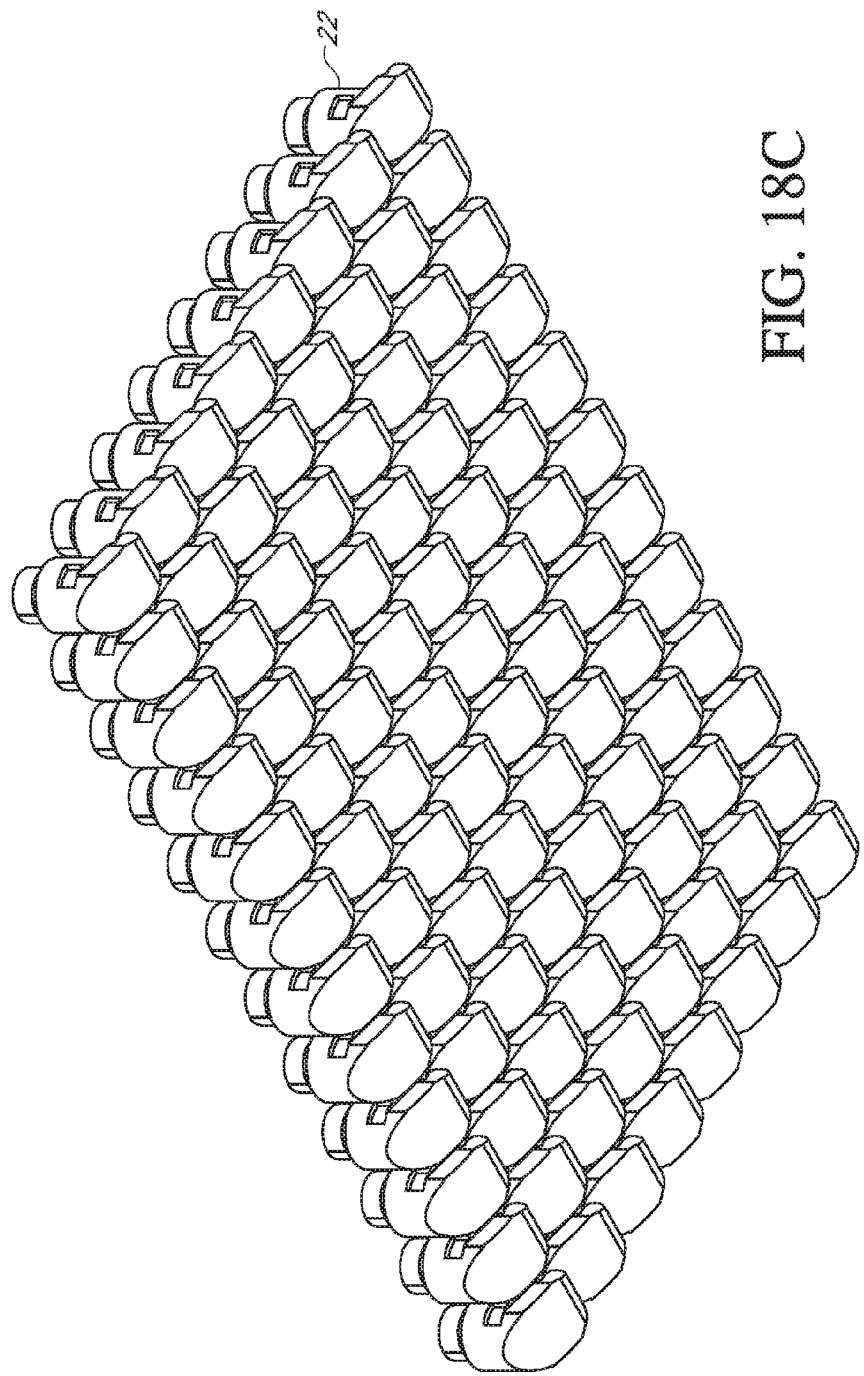
FIG. 18C depicts a three-dimensional view of an array of sample containers of the disclosure arranged in a 96-well format, according to one embodiment of the disclosure.

In some embodiments, apparatus of the disclosure can be used with a multi-well device. For example, samples obtained in sample container 22 of the disclosure can be aligned with multi-well devices, such as 96-wells, 384-wells, 1536 wells and the like. In some embodiments, the sample containers have dimensions that allow them to align onto multi-well plates and can be used to transfer multiple samples onto a multiwell format for simultaneous sample tissue processing or sample testing. An example of sample container 22 of the disclosure fitting onto a 96-well format is shown in FIGS. 18A, 18B and 18C. After tissue extraction and ear-tag 26 application on to ear 25, sample containers 22 can be moved onto multi-well plates as depicted.

Accordingly, devices of the disclosure can be used with a multi-well processing device for simultaneous sample tissue processing or testing after tissue extraction by moving sample containers of the disclosure onto multi-well plates. The asymmetric bottom part of sample containers of the disclosure forms a cut-out or a cavity into which a protrusion of the next container (in a multi-well container configuration) can be positioned into when aligned in a multi-well format, such as a 96-well format, a 384-well format, and/or a 1536 well format. In some embodiments, the footprint of each container can be larger than a diameter of 9 mm and would fit into a multi-well format.

FIG. 18A depicts a two-dimensional view of sample containers 22 of the disclosure arranged in an array with their asymmetrical bottom parts positioned to align with each other as the subsequent container 22 fits into a grove of the asymmetric portion of a previous container according to one embodiment of the disclosure. FIG. 18B depicts the top view of an array of sample containers 22 of the disclosure arranged in a 96-well format. According to one embodiment of the disclosure, FIG. 18B depicts certain exemplary dimensions of sample containers arranged in an array that enable use of the containers of the disclosure in a 96-well format. The dimension of 10.05 mm shows the maximum footprint edge length which is larger than the maximum 9 mm×9 mm edge length allowed by a standard 96-well format. The 9 mm×9 mm dimension depicted in FIG. 18B is to illustrate the maximum dimensions allowed by the 96-well format. The diameter of the main body of the container is 7.2 mm according to this exemplary embodiment. FIG. 18C depicts a three-dimensional view of an array of sample containers 96 of the disclosure arranged in a 96-well format, according to one example embodiment of the disclosure.

One of skill in the art will realize that devices of the disclosure are not limited to devices 10 and 10' as depicted in FIGS. 1-13 and FIGS. 14A-18C, but the present description is to merely illustrate some features of devices of the disclosure.

In some embodiments, a device for attaching an identity tag and removing a tissue sample is described comprising an ear-tag applicator; a means (such as but not limited to flap 16) to hold a sample container below a male part of the identity tag (male tag) and above a female part of the identity tag (female tag); the male tag having a removable tissue cutting element; the removable tissue cutting element having at least a part configured to form a lid on the sample container; at least one holder (16c) reversibly connected to the removable tissue cutting element (punch) 9c; a clamp (18) reversibly connected to the sample container (22); the male tag having a movement path toward the female tag; and at least one part of the sample container or one part of the removable tissue cutting element characterized by a feature that supports movement of the sample container out of the movement path of the male tag, wherein the sample container and the clamp remain in the movement path of the male tag when there is a connection between the holder and the removable tissue cutting element and when there is a connection between the clamp and the sample container, wherein the connection between the holder and the removable tissue cutting element and the connection between the clamp and the sample container are released after a tissue sample is removed but before the male tag part enters the female part, wherein when the connections are released the sample container retains the lid and the sample container with lid move out of the movement path of the male tag.

In some embodiments, the means to hold a sample container below a male tag and above a female tag is a part such as but not limited to flap 16 as described in the drawings. A device of the disclosure can have one or more of several features that can supports movement of the sample container out of the movement path of the male tag. Non limiting examples of such features include an asymmetric bottom of the sample container; and/or a removable tissue cutting element (such as 9c in embodiments of FIGS. 1-13 or parts 9d' and 9e' in embodiments of FIGS. 14A-17B); and/or a part of a removable tissue cutting element or a punch as described herein; and/or a hinge integrated in a punch or cutting element; and/or a multi-part punch (such as shown in FIGS. 14A-17B).

In some embodiments, in a device of the disclosure the release of a clamp is actuated by the position and/or movement of a tissue cutting element (e.g. such as but not limited to a punch, a part of a punch, and/or an intermediate part such as 22' that pushes clamps 18a and 18b to the side).

In some embodiments, in a device of the disclosure the release of a clamp is actuated by a predetermined breaking point on the clamp or the sample container.

In some embodiments, a device of the disclosure can further comprise a flap that connects the sample container to the removable tissue cutting element and male tag. In some embodiments, the flap is connected to the ear-tag applicator/pliers.

In some embodiments, the disclosure describes a device for attaching an identity tag and removing a tissue sample comprising: an ear-tag applicator/pliers; a sample container; a means to hold a male tag part of the identity tag onto portions of the ear-tag applicator; a means to hold a female tag part of the identity tag below the male tag and below the ear, such that the ear is in between the male tag and the female tag; a means to hold the sample container below both the ear and the male tag and above the female tag; the male tag having a tissue cutting element at least a part of which can detach from the male tag after excision of the ear tissue and attach to the sample container to form a lid on the sample container; the device having at least one element that can cause the sample container to move out of the movement path of the male tag following removal of the tissue sample and placement of cut tissue sample into the container and placement of lid onto the sample container such that the male tag portions can move toward and enter the female tag to fit together thereby attaching the ear-tag to the ear.

Non limiting examples of the at least one element that can cause the sample container to move out of the movement path of the male tag following removal of the tissue sample and placement of cut tissue sample into the container and placement of lid onto the sample container are one or more of the following: an asymmetric bottom of the sample container; and/or a removable tissue cutting element (such as 9c in embodiments of FIGS. 1-13 or parts 9d' and 9e' in embodiments of FIGS. 14A-17B); and/or a part of a removable tissue cutting element or a punch as described herein;

and/or a hinge integrated in a punch or cutting element; and/or a multi-part punch (such as shown in FIGS. 14A-17B).

In some embodiments of the device described above, a means to hold a male tag part of the identity tag onto portions of the ear-tag applicator comprises a flap (such as 16 or 16' as described above) and can optionally also comprise a downholder clip.

In some embodiments of the device described above, a means to hold a female tag part of the identity tag below the male tag and below the ear, such that the ear is in between the male tag and the female tag comprises a space, a cavity or a groove on the ear-tag applicator wherein the portions of the female part tag can reversibly fit into.

In some embodiments of the device described above, a means to hold the sample container below both the ear and the male tag and above the female tag comprises a flap (such as 16 or 16' as described above) and may optionally also comprise a downholder clip. In some embodiments, the means to hold the sample container below both the ear and the male tag and above the female tag can further comprise a clamp.

In some embodiments of the device described above, at least a part of the male tag having a tissue cutting element which can detach from the male tag after excision of the ear tissue and attach to the sample container to form a lid on the sample container can comprise the entire tissue cutting element or punch (such as 9*c*) or parts thereof (such as 9*d'* and 9*e'*).

In some embodiments, the disclosure describes a device for attaching an identity tag and removing a tissue sample comprising: an ear-tag applicator/pliers; a sample container; a flap and a downholder clip that are operable to hold: 1) a male tag part of the identity tag onto portions of the ear-tag applicator; and 2) to hold the sample container below both the ear and the male tag and above the female tag; at least one clamp; a female tag part of the identity tag below the male tag and below the ear, such that the ear is in between the male tag and the female tag held in place by a space, a cavity or a groove on the ear-tag applicator wherein the portions of the female part tag can reversibly fit into; the male tag having a tissue cutting element, which in entirety or at least a part of which, can detach from the male tag after excision of the ear tissue and attach to the sample container to form a lid on the sample container; and at least one element that can cause the sample container to move out of the movement path of the male tag following removal of the tissue sample and placement of cut tissue sample into the container and placement of lid onto the sample container such that the male tag portions can move toward and enter the female tag to fit together thereby attaching the ear-tag to the ear.

Non limiting examples of the at least one element that can cause the sample container to move out of the movement path of the male tag following removal of the tissue sample and placement of cut tissue sample into the container and placement of lid onto the sample container are one or more of the following: an asymmetric bottom of the sample container; and/or a removable tissue cutting element (such as 9*c* in embodiments of FIGS. 1-13 or parts 9*d'* and 9*e'* in embodiments of FIGS. 14A-17B); and/or a part of a removable tissue cutting element or a punch as described herein; and/or a hinge integrated in a punch or cutting element; and/or a multi-part punch (such as shown in FIGS. 14A-17B).

In some embodiments of the device described above, a flap can comprise elements such as 16 or 16' as described above and a downholder clip can comprise elements such as 17 or 17'. In some embodiments of the device described above, at least a part of the male tag having a tissue cutting element which can detach from the male tag after excision of the ear tissue and attach to the sample container to form a lid on the sample container can comprise the entire tissue cutting element or punch (such as 9*c*) or parts thereof (such as 9*d'* and 9*e'*).

The present specification also describes methods for attaching an identity tag to an animal and obtaining samples from the animal. In some embodiments an identity-tag attached to an ear using a method and a device of the disclosure cannot be tampered with (i.e., cannot be removed and/or transferred from one animal to another).

Animals to which ear-tags can be attached to by devices and methods of the disclosure include cattle, cows, bison, buffalos, sheep, goats, pigs, deer, reindeer and any wild or domestic animals to which an identity tag is desired to be attached and tissue sample derived for testing.

Samples obtained from an animal can be a tissue sample, an ear sample, a skin sample, a cartilage sample, a blood sample.

A method of the disclosure in some embodiments comprises: reversibly attaching a male-part of an ear-tag (male tag) having a tissue cutting element onto an ear-tag applicator (such as a pliers) in a position above an ear that is to be tagged and from which sample is to be obtained; placing a female part of an ear-tag (female tag) onto or near the ear-tag applicator; placing a sample container having an asymmetrical bottom part in position below the male tag and the ear and above the female tag; moving the male-part of the ear-tag by means of the ear-tag applicator downward toward and through the ear such that the tissue cutting element of the male tag pierces through the ear and places the excised ear tissue into the sample container; continuing to move the male tag downward to the female tag past the sample container such that movement of the male tag moves the sample container transversely out of way of the descending male tag; forming a seal of the male tag and female tag, thereby attaching the ear-tag to the ear and obtaining ear-tissue sample in the sample container.

The ear-tag applicator can be a pliers such as any commercially available ear-tag applicator or an ear-tag applicator as described in the present application.

In some embodiments, the female part of the ear-tag can be placed in a groove of the ear-tag applicator fashioned to receive the female part container. In some embodiments, the female tag can be placed near the ear-tag-applicator by means of clamps, clips or magnetic forces.

In some embodiments of the method, the male tag is attached manually or robotically to the ear-tag-applicator by a pin on the applicator that is movable up and down by means of one or more pliers handles up and down a pivotable axis. In some embodiments, the male tag comprises a hollow stalk inside of which is a complementary shaped element designed to fit into the pin of the ear-tag applicator.

In some embodiments, the sample container is held in place prior to and during piercing of the ear tissue by means of one or more of a downholder clip, one or more clamps and/or a flap. In some embodiments, the asymmetric shape of the sample container at the bottom facilitates the transverse movement of the sample container following movement of the male tag components toward the female tag located directly below the original place of the sample container.

In some embodiments of the method, a lid is placed on the sample container after the excised ear tissue is placed in. In some embodiments, a part of the male-tag detaches to form the sample container lid. In some embodiments, the lid part of the male tag is placed over the sample container while the excised tissue is placed in the sample container. In some embodiments, of the method the lid is an air-tight lid.

In some embodiments, excising ear tissue can comprise one or more methods selected from: piercing ear tissue, punching a hole in the ear tissue, cutting the ear tissue, tearing off the ear tissue.

In some embodiments, a method of the disclosure enables comfortable handling while using a device of the disclosure in the field and lab for removing tissue samples and attaching an ear-tag. For example, a flap of the disclosure that connects together sample container, punch and male tag to the ear-tag applicator. This connection enables a user to simply push a male tag 7 onto pin 6 and attach flap part 20 to a downholder clip 17. Furthermore the connection between a male tag and sample container during packaging prevents mixing-up of samples since typically a container will be labeled with the same animal ID as the ear-tag.

Samples of ear tissue obtained can be taken to a laboratory for testing or tested at the sample excision site by other methods in the art for testing samples. Samples may need to be preserved for testing and transportation and hence a tissue container can contain a desiccant, a preservative, a buffer and the like that can preserve the sample.

The present disclosure also describes kits for attaching an identity-tag to an animal and obtaining tissue samples from the animal. In some embodiments, a kit of the disclosure comprises at least one or more components of device 10 or 10' as described herein. A kit can comprise, for example, flap (such as but not limited to 16 or 16'), a downholder clip (such as but not limited to 17 or 17'), sample container having an asymmetrical base (such as but not limited to 22) and clamp elements (such as but not limited to 18 or 18').

In some embodiments of a kit of the disclosure, sample container can be pre-packaged with a desiccant material, a preservative, and/or a buffer inside it to preserve the tissue sample obtained by the device of the disclosure. A kit can optionally comprise an ear-tag applicator (such as but not limited to pliers 1) as described herein or any other ear-tag applicator pliers available in the market. A kit can optionally comprise ear-tags comprising male and female components.

In some embodiments, a kit of the disclosure will not comprise ear-tag applicators or ear-tags and the user can use the other components of the kit with any ear-tag and ear-tag applicator they have.

Components of a kit of the disclosure can be packaged in one or more container means. In some embodiments desiccants and/or buffer components can be packaged in lyophilized form.

A kit of the disclosure may also comprise one or more reagents for processing the tissue sample and can comprise reagents for extracting, isolating and/or purification of nucleic acids and/or proteins from the sample tissue. A kit may further comprise reagents for downstream processing of an isolated nucleic acids or proteins from tissue by downstream methods such as but not limited to immunoassays, ELISA's PCR, qPCR, real-time PCR and performing assays as set forth above. Accordingly, kits of the disclosure may include without limitation at least one RNase inhibitor; at least one cDNA construction reagents (such as reverse transcriptase); one or more reagents for amplification of RNA, one or more reagents for amplification of DNA including primers, reagents for purification of DNA, probes for detection of specific nucleic acids; primary antibodies, secondary antibodies, immunodetection agents and buffers. A kit of the disclosure may in some embodiments include components for the identification of specific pathogens in a sample comprising primer/probes having sequences specific to the pathogen.

Reagents and components of kits may be comprised in one or more suitable container means. A container means may generally comprise at least one vial, test tube, flask, bottle, syringe or other container means, into which a component may be placed, and preferably, suitably aliquoted. Where there is more than one component in a kit they may be packaged together if suitable or the kit will generally contain a second, third or other additional container into which the additional components may be separately placed. However, in some embodiments, certain combinations of components may be packaged together comprised in one container means. Such containers may include injection or blow-molded plastic containers into which the desired vials are retained.

A kit of the disclosure can also include instructions for employing the kit components and may also have instructions for the use of any other reagent not included in the kit. Instructions can include variations that can be implemented.

EXAMPLES

Aspects of the present teachings can be further understood in light of the following examples, which should not be construed as limiting the scope of the present teachings in any way.

Example 1

Construction & Assembly of Devices

The present Example describes embodiments of devices of the disclosure in relation to FIG. 1. Part numbers used are consistent with those used in FIG. 1. However, one of skill in the art will note that the disclosure is not limited by the examples described here and the examples are merely to illustrate concepts of the disclosure. Similar fabrication, assembly and use methods as described below can be used to make and use devices described in other parts of the specification, including devices described for example in FIGS. 14A-17B as well.

Pliers and Ear-Tag

Pliers (also referred to herein as ear-tag applicators) used is a commercially available standard applicator for ear-tags. Parts 5 and 5' in the pliers used are made of a rigid plastic and can include materials such as but not limited to glass fibers. All other parts of the standard ear-tag applicator (e.g. base, bottom part, top part, pin 6) are made of metal. Ear-tag parts including male part 7 and female part 12 are also commercially available and made of plastic. Downholder clip 17 is also made of metal and is part of a commercially available ear-tag applicator device.

Selective Laser-Sintering

Sample container 22 and clamp 18 were produced by selective laser-sintering using PA12 (polyamide 12) powder reinforced by glass balls. Tissue cutting element (also referred to as removable tissue cutting element, and, in some embodiments, part 9c) was also produced by the same material. To strengthen up the cutting edge of part 9c a metal ring was assembled around the plastic part. For example, a metal ring or metal sleeve was pushed into the lower cavity of the plastic parts of sample container 22. Flap 16 and its components such as one or more of parts 16a, 16b, 16d and 16c were produced by selective laser-sintering using a PA powder resulting in parts with a coefficient of elasticity of 1500 MPA. Although this example describes use of PA12 powder, other similar materials can be used to fabricate a sample container using the teachings described here.

Assembly

A. Pre-Assembly of the Group of Parts Including "Male Tag-Container-Clamp-Flap":

In a first assembly step the flap part 16 (including for example one or more parts of flap including 16, 16b, 16a, 16d, 16c) were connected to container 22 by pushing part of flap 16 into a cavity of container 22. In a second step clamp 18 was connected to container 22 (for example, clicked into position). As a final pre-assembling step of the group "male tag-container-clamp-flap", the tissue cutting element (9c) was put on part 11 of the male tag and fixed in position by holder and/or arms 16c.

B. Assembly of Applicator-Ear-Tag-Sampling-Device:

First male tag 7 was pushed onto pin 6 of the applicator. In a second step arms 20 of flap 16 were pushed into the socket of clip 17. As the last assembly step, female tag 12 is put into the groove/space/cavity 1d of the ear-tag applicator. The position of the container 22 above the female tag 12 is defined by the flap length between arms 20 and container 22.

Example 2

Application of Ear-Tag and Tissue Sampling

Robustness of Device Component Alignment:

The first experiments were done without an ear to test the correctness and robustness of the alignment of device components before and during the application of the ear-tag and tissue sampling. To test the robustness of the connection between container 22 and clamp 18 a rigid piece of plastic with 3 mm thickness was put between the container 22 and the male tag 7 to simulate a thick ear that cannot be penetrated. Even when a lot of hand force is applied on the ear-tag applicator handles 5 and 5' to close the ear-tag applicator 10, the connection between container 22 and clamp 18 did not fail. This shows that the connection between the container and clamp is robust enough to ensure tissue sampling and that container 22 will not slip away transversally before a tissue sample and tissue cutting element (punch) or parts thereof are securely introduced in the container (i.e., tissue sample is placed in container and tissue cutting element on the male tag is introduced into container as its lid).

Functioning of Device:

A second experiment was done without an ear and without any material between container and male tag/punch. When the punch (tissue cutting element of male tag 7) pushed the part 16b' down, the part 16b' transversally moved the clamp 18. When the punch is inside the container 22 as a lid, part 16b' transversally moved the clamp until it no longer supports the container. When this happens the container slips transversally with its asymmetric bottom on the surface of the female tag as the male tag is further moved towards the female tag. Finally the male tag is locked to the female tag and the container is closed by the punch which forms a container lid.

Sample Extraction and Ear-Tag Application:

Experiments with a calf ear showed that the container and clamp connection (as described above) indeed is robust enough to ensure that calf ear tissue can be cut between the punch (of the male tag) and the top edge of the container without any displacement or movement of the container during cutting. The container is only displaced (moves/slips transversally) when the cut ear tissue sample and the punch are introduced into the container and the punch has pushed the clamp aside (such as by means of the part 16b' that holds the container to the flap 16 and clamp 18). The present experiments as described above show that devices of the disclosure work reliably.

Each embodiment disclosed herein may be used or otherwise combined with any of the other embodiments disclosed. Any element of any embodiment may be used in any embodiment. Although the invention has been described with reference to specific embodiments, it will be understood by those skilled in the art that various changes may be made and equivalents may be substituted for elements thereof without departing from the true spirit and scope of the invention. In addition, modification may be made without departing from the essential teachings of the invention.

What is claimed:

1. A device for attaching an identity tag and removing a tissue sample comprising:
    an ear-tag applicator;
    a means to hold a sample container below a male part of the identity tag (male tag) and above a female part of the identity tag (female tag) and below an ear to which the identity tag is to be attached and from which tissue sample is to be removed;
    the male tag having a removable tissue cutting element;
    at least one holder reversibly connected to the removable tissue cutting element and a clamp reversibly connected to the sample container;
    the male tag having a movement path toward the female tag; and
    at least one part of the sample container or one part of the removable tissue cutting element having a feature that supports movement of the sample container out of the movement path of the male tag,
    wherein the sample container and the clamp remain in the movement path of the male tag when there is a connection between the holder and the removable tissue cutting element or when there is a connection between the clamp and the sample container or when both the connection between the holder and the removable tissue cutting element and the connection between the clamp and the sample container are present,
    wherein the connection between the holder and the removable tissue cutting element and/or the connection between the clamp and the sample container are released after a tissue sample is removed but before the male tag part enters the female part,
    wherein when the connection between the holder and the removable tissue cutting element and/or the connection between the clamp and the sample container are released the sample container retains the removable tissue cutting element or at least a part thereof and the sample container moves out of the movement path of the male tag.

2. The device of claim 1, wherein the feature that supports movement of the sample container out of the movement path of the male tag is: an asymmetric bottom of the sample container, a slit in the removable tissue cutting element a hinge integrated in the removable cutting element, a part of the removable tissue cutting element wherein the removable tissue cutting element is made up of more than one parts and any combination of the above.

3. The device of claim 1, wherein the means to hold the sample container below the male tag and above the female tag is a flap.

4. The device of claim 3, wherein the flap further connects the sample container to the male tag.

5. The device of claim 3, wherein the flap is further connected to the ear-tag applicator.

6. The device of claim 3, wherein the at least one holder is a part of the flap.

7. The device of claim 3, wherein the flap is fabricated by selective laser-sintering.

8. The device of claim 1, wherein the clamp and the sample container are fabricated by selective laser-sintering.

9. The device of claim 1, wherein the removable tissue cutting element or part thereof that is retained by the sample container after the connections are released forms a lid on the sample container.

10. A device for attaching an identity tag and removing a tissue sample comprising:
an ear-tag applicator;
a sample container;
a means to hold a male tag part of the identity tag onto portions of the ear-tag applicator;
a means to hold a female tag part of the identity tag below the male tag and below the ear;
a means to hold a sample container below both the ear and the male tag and above the female tag;
the male tag having a tissue cutting element at least a part of which can detach from the male tag after excision of the ear tissue and attach to the sample container; and
at least one element that can cause the sample container to move out of the path of movement the male tag, following removal of the tissue sample and placement of cut tissue sample into the container and detachment of tissue cutting element or a part thereof, such that the male tag can move toward and enter the female tag to fit together thereby attaching the ear-tag to the ear.

11. The device of claim 10, wherein the at least one element that can cause the sample container to move out of the movement path of the male tag, following removal of the tissue sample and placement of cut tissue sample into the container and detachment of removable cutting element, is: an asymmetric bottom of the sample container, the tissue cutting element, a part of the tissue cutting element, a hinge integrated in the tissue cutting element, or any combination thereof.

12. The device of claim 10,
wherein, the means to hold a male tag part of the identity tag onto portions of the ear-tag applicator comprises:
a flap;
a pin on the ear-tag applicator; and
optionally further comprises a downholder clip; and
wherein, the means to hold the sample container below both the ear and the male tag and above the female tag comprises:
the flap;
a clamp; and
optionally further comprises the downholder clip.

13. The device of claim 10, wherein the means to hold the female tag part of the identity tag below the male tag and below the ear is a space, a cavity or a groove on the ear-tag applicator into which portions of the female tag part can reversibly fit into.

14. The device of claim 10, wherein the ear-tag applicator is a pliers, a modified pliers or a commercial ear-tag applicator.

15. The device of claim 10, wherein the sample container comprises a chamber for storing excised tissue.

16. The device of claim 10, wherein the sample container contains a desiccant, a preservative, a buffer or any combinations thereof.

17. The device of claim 10, wherein the tissue cutting element or part thereof which detach from the male tag after excision of the ear tissue further attaches to the sample container to form a lid on the sample container.

18. The device of claim 10, wherein the pin on the ear-tag applicator is movable up and down by movement of one or more plier handles about a pivotable axis on the ear-tag applicator; and the pin on the ear-tag applicator has a part shaped to have a complementary fit with a structure in the male tag.

\* \* \* \* \*